(12) United States Patent
Lawler et al.

(10) Patent No.: US 11,141,404 B1
(45) Date of Patent: Oct. 12, 2021

(54) FORMULATIONS AND METHODS FOR TREATING ACUTE CANNABINOID OVERDOSE

(71) Applicant: Anebulo Pharmaceuticals, Inc., Lakeway, TX (US)

(72) Inventors: Joseph Fenton Lawler, Lakeway, TX (US); Daniel Pawel Schneeberger, Austin, TX (US)

(73) Assignee: ANEBULO PHARMACEUTICALS, INC., Lakeway, TX (US)

( * ) Notice: Subject to any disclaimer, the term of this patent is extended or adjusted under 35 U.S.C. 154(b) by 0 days.

(21) Appl. No.: 17/100,157

(22) Filed: Nov. 20, 2020

Related U.S. Application Data

(60) Provisional application No. 63/115,487, filed on Nov. 18, 2020.

(51) Int. Cl.
| | |
|---|---|
| *A61K 31/397* | (2006.01) |
| *A61K 9/02* | (2006.01) |
| *A61K 9/06* | (2006.01) |
| *A61K 9/19* | (2006.01) |
| *A61K 9/00* | (2006.01) |
| *A61K 9/70* | (2006.01) |

(52) U.S. Cl.
CPC ............ *A61K 31/397* (2013.01); *A61K 9/006* (2013.01); *A61K 9/0019* (2013.01); *A61K 9/0073* (2013.01); *A61K 9/02* (2013.01); *A61K 9/7023* (2013.01)

(58) Field of Classification Search
CPC .. A61K 31/485; A61K 9/0053; A61K 31/137; A61K 31/138; A61K 31/4748; A61K 31/397; A61K 9/02; A61K 9/7023; A61K 9/0073; A61K 9/006; A61K 9/0019
See application file for complete search history.

(56) References Cited

U.S. PATENT DOCUMENTS

| | | |
|---|---|---|
| 6,403,574 B1 | 6/2002 | Adams et al. |
| 6,566,356 B2 | 5/2003 | Achard et al. |
| 7,504,522 B2 | 3/2009 | Davidson et al. |
| 8,450,346 B2 | 5/2013 | Roughley et al. |
| 8,835,418 B2 | 9/2014 | Bartsch et al. |
| 10,570,146 B2 | 2/2020 | Makriyannis et al. |
| 2006/0276452 A1 | 12/2006 | Davidson et al. |
| 2007/0054891 A1* | 3/2007 | Davidson ............... A61P 25/00 514/210.17 |
| 2007/0173486 A1 | 7/2007 | Davidson et al. |
| 2009/0181939 A1 | 7/2009 | Davidson et al. |
| 2020/0179271 A1 | 6/2020 | Skolnick |
| 2020/0397749 A1* | 12/2020 | Skolnick ............... A61K 31/397 |

FOREIGN PATENT DOCUMENTS

| | | |
|---|---|---|
| WO | WO-0107023 A2 | 2/2001 |
| WO | WO-2018204689 A1 | 11/2018 |
| WO | WO-2020118048 A1 | 6/2020 |

OTHER PUBLICATIONS

Kelly et al., Cannabinoid Toxicity, StatPearls Publishing, LLC, Aug. 23, 2020.*
Lee et al., "Plasma Cannabinoid Pharmacokinetics After Controlled Smoking and Ad libitum Cannabis Smoking in Chronic Frequent Users," J Anal Toxicol. Oct. 2015; 39(8):580-587.*
Ismaili et al., "The Oral Cannabis Poisoning of the Children," Chemical Sciences Journal, 2014, 5:1.*
Fong et al., "Pharmacological Efficacy and Safety Profile of Taranabant in Preclinical Species," Drug Development Research 70: 349-362 (2009).*
FDA Briefing Document. NDA 21-888. Zimulti (rimonabant) Tablets, 20 mg. Sanofi Aventis. Advisory Committee (2007) http://online.wsj.com/public/resources/documents/fdaacomplia20070611.pdf.
Nathan et al.: Neuropsychiatric Adverse Effects of Centrally Acting Antiobesity Drugs. CNS Neurosci. Ther. 17:490-505 (2011).
P. Skolnick (lead investigator): Development of Drinabant for Treatment of Acute Cannabinoid Overdose. National Institutes of Health BrIDGs Project, published online Nov. 2, 2020.
Turpault et al.: Rimonabant pharmacokinetics in healthy and obese subjects. Am. Soc. for Clin. Pharm. and Ther. (2005) 79:P50-P50, published Feb. 28, 2006.
Zuurman et al.: Inhibition of THC-induced effects of the central nervous system and heart rate by a novel CB1 receptor antagonist AVE1625. J. Psychopharm., 24:363 (2010).
Jones, End of the line for cannabinoid receptor 1 as an anti-obesity target? Nature Reviews 7: 961-962 (2008).
Koch, Taranabant no longer developed as an antiobesity agent. Nature Reviews 6: 300 (2010).
Myers, Merck Discontinues Development of Investigational Medicine Taranabant for Obesity. Fierce Biotech 4 pages (2008).

* cited by examiner

*Primary Examiner* — Jared Barsky
(74) *Attorney, Agent, or Firm* — Wilson Sonsini Goodrich & Rosati

(57) ABSTRACT

Described herein are uses of the CB1 inhibitors (e.g., antagonists, neutral antagonists, inverse agonists) and various methods of using and administering a CB1 inhibitor to a patient, especially patients showing symptoms of drug overdose or suspected of a drug overdose. Further described herein are uses wherein the CB1 inhibitor is ANEB-001. Further described herein are treatments with a CB1 inhibitor for THC or synthetic cannabinoid overdose.

16 Claims, 1 Drawing Sheet

FORMULATIONS AND METHODS FOR TREATING ACUTE CANNABINOID OVERDOSE

CROSS-REFERENCE

This application claims the benefit of U.S. Provisional Patent Application No. 63/115,487 filed on Nov. 18, 2020, which is incorporated herein by reference in its entirety.

BACKGROUND

The widespread use of α9-tetrahydrocannabinol (THC) and synthetic cannabinoids (SCs) has resulted in an increased number of emergency room visits secondary to symptoms of cannabinoid overdose; this is especially notable after cannabis is legalized in a jurisdiction. A medical need therefore exists to treat THC and SC related-overdoses.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

BRIEF SUMMARY

Figure 1:
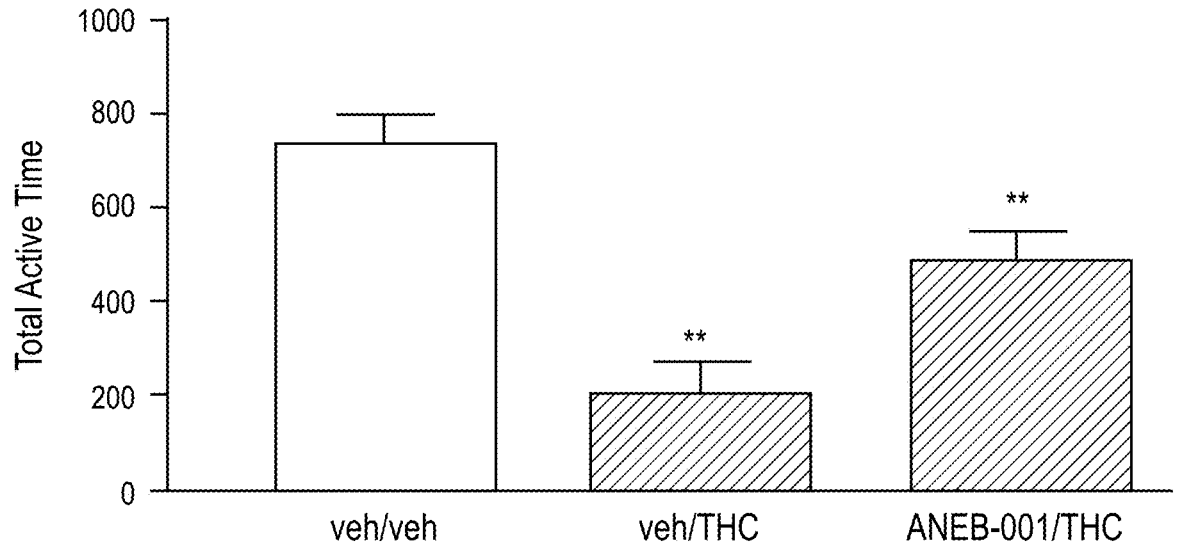
FIG. 1 illustrates a plot of the effect of ANEB-001 on THC-induced hypolocomotion in mice. The total active time is plotted against conditions of vehicle only, treatment with THC, and treatment with ANEB-001 and THC. veh: vehicle; THC: tetrahydrocannabinol.

Described herein are compositions, formulations, methods, and devices for treating THC and SC overdose. In some embodiments, the overdose is an acute overdose. In some embodiments, methods described herein comprise use of a CB1 inhibitor. Accordingly, described herein are compositions, formulations, and methods for reversing the symptoms of cannabinoid overdose using the CB1 antagonist ANEB-001, or a salt, adjunct, or polymorph thereof. Other aspects of the compositions and methods described herein are described below or throughout this specification.

Provided herein are methods of using a pharmaceutical composition comprising a CB1 inhibitor, the method comprising administering to a patient an effective amount of the CB1 inhibitor and a pharmaceutically acceptable carrier or excipient, wherein the patient has a known or suspected acute drug overdose reaction. Provided herein are methods of using a pharmaceutical composition comprising a CB1 inhibitor, the method comprising administering to a patient an effective amount of the CB1 inhibitor and a pharmaceutically acceptable carrier or excipient, wherein the patient has a known or suspected acute drug overdose reaction, wherein the CB1 inhibitor has the structure of formula (I):

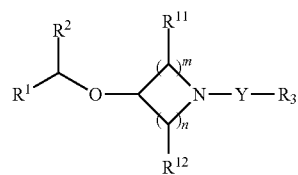

formula (I), or a pharmaceutically acceptable salt or prodrug thereof, wherein $R^1$ is aryl or heteroaryl;

$R^2$ is alkyl, aryl or heteroaryl;

$R^3$ is alkyl, aryl, heteroaryl, $NR^9R^{10}$, $OR^{15}$, or $NR^{16}C(O)R^{17}$;

Y is C=O, C=S, $SO_2$, or $(CR^7R^8)_p$;

$R^7$ and $R^8$ are independently selected from H and lower alkyl;

$R^9$ is selected from H, alkyl, aryl, heteroaryl, and non-aromatic heterocyclic groups, or together with $R^{10}$ forms a saturated 4, 5, 6, or 7 membered ring optionally containing an additional heteroatom selected from N and O;

$R^{10}$ is selected from H and lower alkyl, or together with $R^9$ forms a saturated 4, 5, 6, or 7 membered ring optionally containing an additional heteroatom selected from N and O;

$R^{11}$ and $R^{12}$ are independently selected from H and lower alkyl;

$R^{15}$ is selected from alkyl and aryl;

$R^{16}$ is selected from H and lower alkyl;

$R^{17}$ is selected from alkyl, aryl, and heteroaryl;

m is 1 or 2;

n is 1 or 2; and p is 1, 2, 3 or 4. Further provided herein are methods wherein m is 1 and n is 1. Further provided herein are methods wherein $R^1$ and $R^2$ are independently aryl. Further provided herein are methods wherein at least one of $R^1$ and $R^2$ has a non-hydrogen substituent in the ortho-position(s) thereof relative to the point of attachment to the [—CH—O—] group. Further provided herein are methods wherein $R^{11}$ and $R^{12}$ are hydrogen. Further provided herein are methods wherein $R^3$ is $NR^9R^{10}$, and $R^9$ and $R^{10}$ are independently lower alkyl or hydrogen. Further provided herein are methods wherein the CB1 inhibitor comprises the structure of formula (Ia):

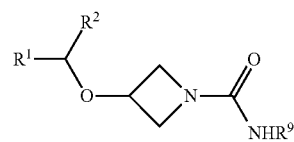

formula (Ia), or a pharmaceutically acceptable salt or prodrug thereof. Further provided herein are methods wherein $R^1$ and $R^2$ are independently selected from a group of formula (II):

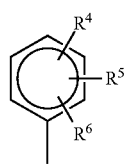

formula (II),
wherein
$R^4$, $R^5$, and $R^6$ are independently selected from hydrogen, halo, alkyl (including haloalkyl), thioalkyl, alkoxy (including haloalkoxy), alkylsulfonyl, amino, mono- and di-alkyl amino, mono- and di-aryl amino, alkylarylamino, aminoalkyl, alkylaminoalkyl, dialkylaminoalkyl, $NR^{14}C(O)R^{19}$, $NR^{14}SO_2R^{20}$, $COOR^{19}$, $OC(O)R^{20}$, $CONR^{13}R^{14}$ and $SO_2NR^{13}R^{14}$, $R^{13}$ and $R^{14}$ are independently selected from hydrogen and alkyl or form a 5 or 6 membered ring optionally containing 1 or 2 additional heteroatoms selected from N, O, and S; $R^{19}$ is selected from H, alkyl, aryl and heteroaryl, and $R^{20}$ is selected from alkyl, aryl and heteroaryl. Further provided herein are methods wherein at least one of $R^4$, $R^5$, and $R^6$ are chloro or trifluoromethyl. Further provided herein are methods wherein the patient shows signs of an acute cannabinoid overdose. Further provided herein are methods wherein the patient shows signs of cannabinoid hyperemesis syndrome. Further provided herein are methods wherein the method comprises treatment for drug overdose prior to treatment with the CB1 inhibitor. Further provided herein are methods wherein the prior treatment comprises one or more of administration of an opiate antagonist, activated charcoal, or emetic. Further provided herein are methods wherein the prior treatment comprises one or more of orogastric lavage or whole bowel irrigation. Further provided herein are methods wherein the method further comprises a diagnostic test prior to treatment with the CB1 inhibitor. Further provided herein are methods wherein the diagnostic test is a blood test. Further provided herein are methods wherein the patient has a cannabinoid plasma concentration of at least 50 μg/L. Further provided herein are methods wherein the patient has a cannabinoid plasma concentration of at least 100 μg/L. Further provided herein are methods wherein the patient has a cannabinoid plasma concentration of 50 μg/L to 300 μg/L. Further provided herein are methods wherein the pharmaceutical composition is prepared as an oral, sublingual, buccal, rectal, nasal, or parenteral dose. Further provided herein are methods wherein the CB1 inhibitor is cannabigerol, ibipinabant, otenabant, tetrahydrocannabivarin, virodhamine, rimonabant, or taranabant. Further provided herein are methods wherein the CB1 inhibitor has the structure:

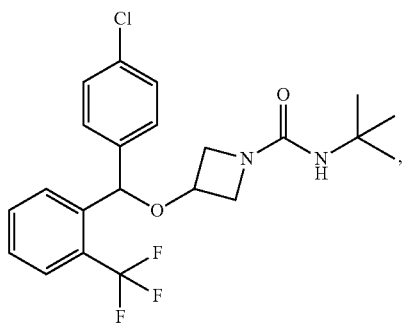

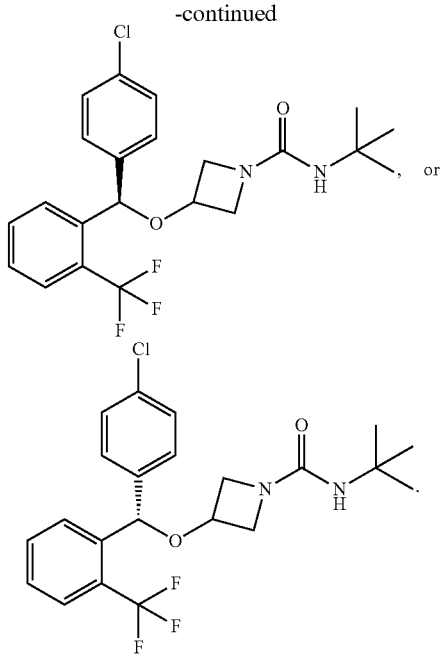

Further provided herein are methods wherein the dose of the CB1 inhibitor is 1 mg to 200 mg. Further provided herein are methods wherein the dose of the CB1 inhibitor is 25 mg to 200 mg. Further provided herein are methods wherein the CB1 inhibitor is formulated as an oral, parenteral, intravenous (IV), intramuscular (IM), subcutaneous (SC), endotracheal, sublingual, buccal, intralingual, submental, transdermal, suppository, or intranasal administration. Further provided herein are methods wherein further comprising administering a pharmaceutically acceptable alkaline agent. Further provided herein are methods wherein the pharmaceutical composition is formulated to deliver an effective dose of the CB1 inhibitor in no more than 10 min.

Provided herein are methods of using a CB1 inhibitor as a pre-exposure prophylactic therapy comprising administering an effective amount of the CB1 inhibitor prior to exposure to a cannabinoid. Further provided herein are methods wherein the cannabinoid is tetrahydrocannabinol. Further provided herein are methods wherein CB1 inhibitor is formulated for oral, parenteral, intravenous (IV), intramuscular (WI), subcutaneous (SC), endotracheal, sublingual, buccal, intralingual, submental, transdermal, suppository, or intranasal administration. Further provided herein are methods wherein the CB1 inhibitor has the structure:

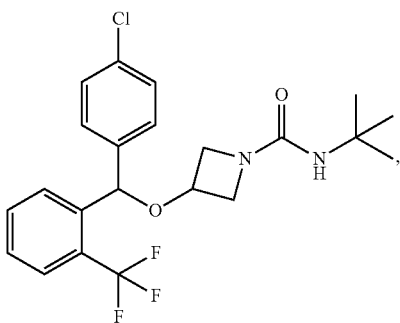

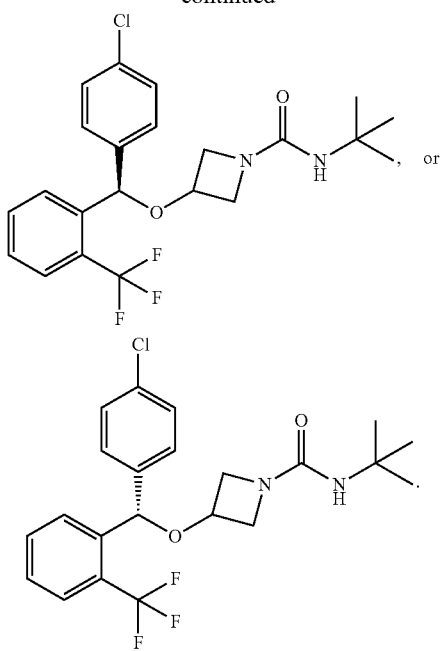

Further provided herein are methods wherein the dose of the CB1 inhibitor is 1 mg to 200 mg. Further provided herein are methods wherein the dose of the CB1 inhibitor is 25 mg to 200 mg.

Provided herein are methods of treating a patient suspected of a drug overdose comprising administering an effective amount of a CB1 inhibitor to a patient and monitoring the patient for reduced symptoms associated with overdose. Further provided herein are methods wherein monitoring comprises monitoring heart rate or respiration. Further provided herein are methods wherein the CB1 inhibitor has the structure:

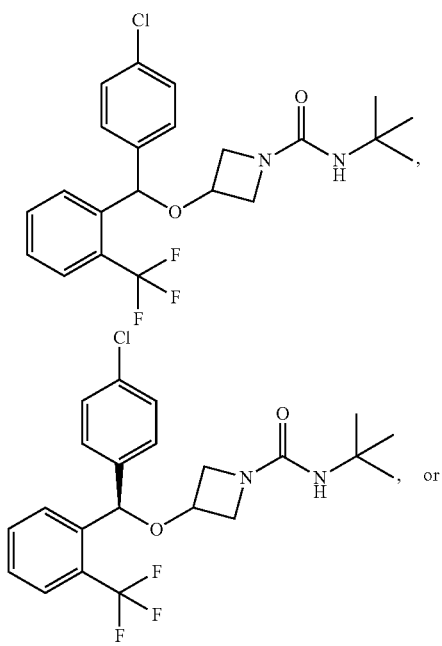

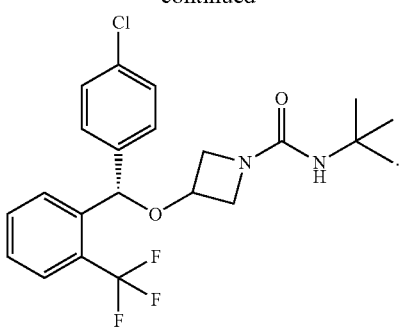

Further provided herein are methods wherein the dose of the CB1 inhibitor is 1 mg to 200 mg. Further provided herein are methods wherein the dose of the CB1 inhibitor is 25 mg to 200 mg.

Provided herein are injectable compositions for treating a suspected drug overdose, the composition comprising a CB1 inhibitor, an opioid antagonist, and a benzodiazepine antagonist. Further provided herein are methods wherein the benzodiazepine antagonist is flumazenil. Further provided herein are methods wherein the opioid antagonist is naloxone. Further provided herein are methods wherein the injectable composition is formulated in a single dose injectable device. Further provided herein are methods wherein the CB1 inhibitor has the structure

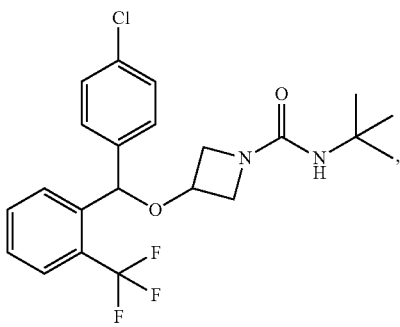

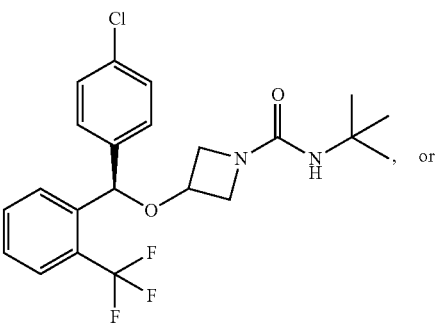

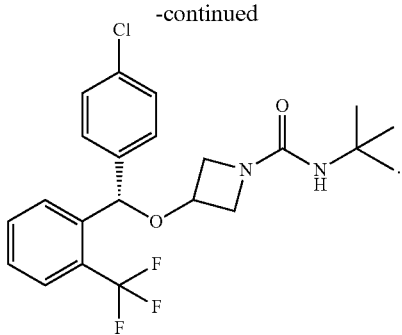

Further provided herein are methods wherein the dose of the CB1 inhibitor is 1 mg to 200 mg. Further provided herein are methods wherein the dose of the CB1 inhibitor is 25 mg to 200 mg.

Provided herein are compositions for treating a suspected drug overdose, the composition comprising a CB1 inhibitor and an anxiolytic agent. Further provided herein are methods wherein the anxiolytic agent is a cannabinoid. Further provided herein are methods wherein the cannabinoid is cannabidiol. Further provided herein are methods wherein composition is formulated for intranasal delivery. Further provided herein are methods wherein the CB1 inhibitor has the structure

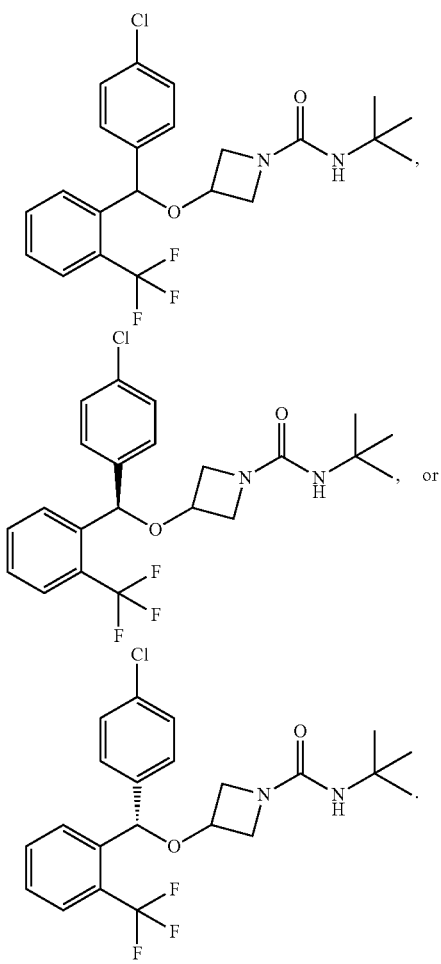

Further provided herein are methods wherein the dose of the CB1 inhibitor is 1 mg to 200 mg. Further provided herein are methods wherein the dose of the CB1 inhibitor is 25 mg to 200 mg.

DETAILED DESCRIPTION

Described herein are compositions, formulations, and methods for reversing cannabinoid overdose and/or one or more symptoms thereof comprising administering a CB1 inhibitor in an amount sufficient to reduce the severity of one or more overdose symptoms or reverse the cannabinoid overdose in a patient. Further described herein are fast-acting formulations comprising CB1 inhibitors for emergency/rescue applications. Further described herein are formulations comprising combinations of CB1 inhibitors and other active agents.

CB1 Inhibitors

Compositions, formulations, and methods described herein may comprise use of a CB1 inhibitor. In some embodiments, the CB1 inhibitor is a CB1 antagonist. In some embodiments, the CB1 inhibitor is a CB1 inverse agonist. In some embodiments, the CB1 inhibitor is a CB1 neutral antagonist. Certain embodiments include the use of the CB1 antagonist and a specific cannabinoid antagonist.

Provided herein compounds having the structure of formula (I):

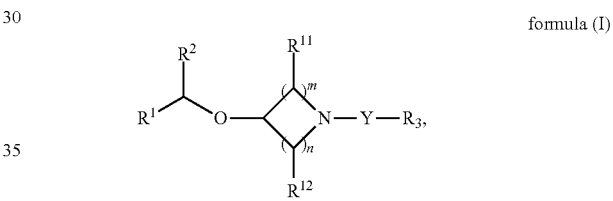

formula (I)

wherein
$R^1$ is aryl or heteroaryl;
$R^2$ is alkyl, aryl or heteroaryl;
$R^3$ is alkyl, aryl, heteroaryl, $NR^9R^{10}$, $OR^{15}$, or $NR^{16}C(O)R^{17}$;
Y is C=O, C=S, $SO_2$, or $(CR^7R^8)_p$;
$R^7$ and $R^8$ are independently selected from H and lower alkyl;
$R^9$ is selected from H, alkyl, aryl, heteroaryl, and non-aromatic heterocyclic groups, or together with $R^{10}$ forms a saturated 4, 5, 6, or 7 membered ring optionally containing an additional heteroatom selected from N and O;
$R^{10}$ is selected from H and lower alkyl, or together with $R^9$ forms a saturated 4, 5, 6, or 7 membered ring optionally containing an additional heteroatom selected from N and O;
$R^{11}$ and $R^{12}$ are independently selected from H and lower alkyl;
$R^{15}$ is selected from alkyl and aryl;
$R^{16}$ is selected from H and lower alkyl;
$R^{17}$ is selected from alkyl, aryl and heteroaryl;
m is 1 or 2;
n is 1 or 2; and
p is 1, 2, 3 or 4.

In some embodiments, $R^1$ and/or $R^2$ is substituted with 1 to 3 substituents. In some embodiments, $R^1$ and/or $R^2$ is substituted with 1 or 2 substituents. In one embodiment, $R^1$ and $R^2$ are independently selected from a group -$A(R^4)(R^5)(R^6)$, where A is an aryl or heteroaryl ring, and where A may be selected from phenyl, naphthyl, thienyl, furanyl, pyrrolyl, imidazolyl, pyrazolyl, thiazolyl, isothiazolyl, oxazolyl, isooxazolyl, pyridyl, pyrazinyl, pyrimidinyl, quinolinyl, isoquinolinyl, benzofuranyl and isobenzofuryl. In some embodiments, one of $R^1$ and $R^2$ is aryl and the other is heteroaryl, or both $R^1$ and $R^2$ are aryl. In some embodiments, both $R^1$ and $R^2$ are monocyclic. In this embodiment, $R^4$, $R^5$, and $R^6$ are independently selected from hydrogen, halo, alkyl (including haloalkyl), thioalkyl, alkoxy (including haloalkoxy), alkylsulfonyl, amino, mono- and di-alkyl amino, mono- and di-aryl amino, alkylarylamino, aminoalkyl, alkylaminoalkyl, dialkylaminoalkyl, $NR^{14}C(O)R^{19}$, $NR^{14}SO_2R^{20}$, $COOR^{19}$, $OC(O)R^{20}$, $CONR^{13}R^{14}$ and $SO_2NR^{13}R^{14}$, wherein $R^{13}$ and $R^{14}$ are independently selected from hydrogen and alkyl or may form a 5 or 6 membered ring optionally containing 1 or 2 additional heteroatoms selected from N, O and S; and $R^{19}$ is selected from H, alkyl, aryl and heteroaryl and $R^{20}$ is selected from alkyl, aryl and heteroaryl. The groups $R^1$ and $R^2$ may be the same or different, and in one embodiment are different. In some embodiments, $R^3$ is $NR^9R^{10}$. In some embodiments, $R^3$ is $NR^9R^{10}$, and $R^9$ and $R^{1'0}$ are independently lower alkyl or hydrogen. In some embodiments, Y is C=O. In some embodiments, Y is C=O and $R^3$ is $NR^9R^{10}$. In some embodiments, $R^3$ is $NR^9R^{10}$, $R^9$ is lower alkyl, and $R^{10}$ is hydrogen.

In some embodiments of a compound of Formula (I) where $R^4$, $R^5$, and $R^6$ are selected from halo. In some embodiments, the halo group is fluoro, chloro, bromo or iodo. In some embodiments, the halo group is chloro or bromo. In some embodiments, $R^4$, $R^5$, and $R^6$ are selected from alkyl, thioalkyl, alkoxy and alkylsulfonyl. In some embodiments, $R^4$, $R^5$, and $R^6$ are selected from lower alkyl. In some embodiments, $R^4$, $R^5$, and $R^6$ are selected from methyl and ethyl. Where $R^4$, $R^5$, and $R^6$ are selected from haloalkyl, the alkyl is in some embodiments methyl, and the $R^4$, $R^5$, or $R^6$ group is trifluoromethyl. Where $R^4$, $R^5$, and $R^6$ are selected from haloalkoxy, the alkyl is in some embodiments methyl and the $R^4$, $R^5$, or $R^6$ group is trifluoromethoxy or difluoromethoxy. In some embodiments, one or two of $R^4$, $R^5$, and $R^6$ are hydrogen. In some embodiments, at least one of the $R^1$ and $R^2$ groups has a non-hydrogen substituent in the ortho-position(s) relative to the point of attachment to the [—CH—O—] group. The $R^1$ or $R^2$ groups may independently have one or two non-hydrogen substituents in said ortho position(s). Preferred ortho-substituents include halo and haloalkyl, as described herein. In some embodiments, ortho-substituents are chloro and trifluoromethyl. In some embodiments, if —Y—$R^3$ is —C(O)NH(alkyl) then: $R^1$ and/or $R^2$ is selected from heteroaryl; and/or m and/or n is 2; and/or $R^{11}$ and/or $R^{12}$ is lower alkyl. In some embodiments, if —Y—$R^3$ is —C(O)NH(alkyl) then: $R^1$ and/or $R^2$ is selected from aryl, and m and n are 1.

In some embodiments of a compound of Formula (I) where $R^{13}$ and $R^{14}$ form a 5- or 6-membered ring, the ring is 6-membered. In some embodiments, the ring is saturated or partially saturated. In some embodiments where the ring contains additional heteroatoms, such as N and O. In some embodiments, there are 0 or 1 additional heteroatoms.

In some embodiments of a compound of Formula (I), $R^1$ is selected from aryl. In some embodiments, $R^2$ is selected from aryl or heteroaryl. In some embodiments, $R^3$ is selected from $NR^9R^{10}$. In an alternative embodiment $R^3$ is selected from alkyl, aryl and heteroaryl. In some embodiments, Y is selected from C=O, C=S and $SO_2$. Where Y is selected from $(CR^7R^8)_p$, then $R^7$ and/or $R^8$ in some embodiments are hydrogen or methyl, and p is 1 or 2. Where Y is $SO_2$, $R^3$ is in some embodiments selected from alkyl, aryl and heteroaryl. Where Y is $(CR^7R^8)_p$, in some embodiments p is 1, and $R^3$ is selected from alkyl, aryl, heteroaryl. In some embodiments, $R^9$ is selected from piperidinyl (such as 1-piperidinyl) and morpholinyl (such as 4-morpholinyl). In some embodiments, $R^9$ is cyclic, such as aryl or heteroaryl, and the $R^9$ group may be substituted with one or more substituent groups. In some embodiments, $R^9$ is substituted with halo, nitro, or alkoxy haloalkyl.

In some embodiments of a compound of Formula (I), the ring formed by $NR^9R^{10}$ may be substituted, and substituents include hydroxy, methoxy, mono- and di-alkyl amino and alkoxycarbonyl. In one embodiment (hereinafter referred to as embodiment (i)), $R^9$ is selected from aryl, heteroaryl and a non-aromatic heterocyclic group, and $R^{10}$ is selected from H and lower alkyl. In an alternative embodiment (hereinafter referred to as embodiment (ii)), $R^9$ is selected from alkyl and $R^{10}$ is selected from lower alkyl. In a further alternative embodiment hereinafter referred to as embodiment (iii)), $R^9$ and $R^{10}$ form a 4, 5, 6, or 7-membered ring, or a 5, 6, or 7-membered ring, optionally containing an additional heteroatom selected from N and 0.

In some embodiments of a compound of Formula (I), m is 1 and/or n is 1. In some embodiments, both m and n are 1. Where m is 2, the $R^{11}$ groups may be the same or different, but at least one of the $R^{11}$ groups in the $(CHR^{11})_2$ moiety is hydrogen. Where n is 2, the $R^{12}$ groups may be the same or different, but at least one and optionally both of the $R^{12}$ groups in the $(CHR^{12})_2$ moiety is/are hydrogen. In some embodiments, $R^{11}$ and $R^{12}$ are independently selected from hydrogen and methyl. In some embodiments, at least one of $R^{11}$ and $R^{12}$ is hydrogen. In some embodiments, $R^{15}$ is selected from alkyl, such as lower alkyl (substituted or unsubstituted). In some embodiments, $R^{15}$ is selected from aryl, such as phenyl (substituted or unsubstituted). In one embodiment, $R^{15}$ is selected from lower alkyl, benzyl and phenyl. In some embodiments, $R^{16}$ is hydrogen. In some embodiments, $R^{17}$ is lower alkyl, aryl, or heteroaryl, and in one embodiment is aryl.

Provided herein are compounds having the structure of formula (Ia)

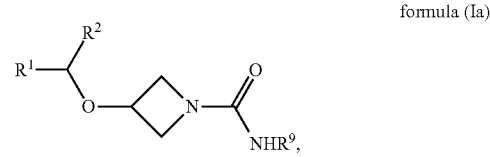

formula (Ia)

or a pharmaceutically acceptable salt or prodrug thereof, wherein
$R^1$ and $R^2$ are independently selected from aryl or heteroaryl; and
$R^9$ is hydrogen or alkyl;
wherein at least one of $R^1$ and $R^2$ has a non-hydrogen substituent in the ortho-position(s) thereof relative to the point of attachment to the [—CH—O—] group.

Provided herein are compounds having the structure of formula (Ia)

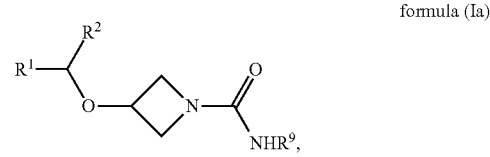

formula (Ia)

or a pharmaceutically acceptable salt or prodrug thereof,
wherein
$R^1$ and $R^2$ are independently selected from aryl; and
$R^9$ is hydrogen or alkyl;
wherein at least one of $R^1$ and $R^2$ has a non-hydrogen substituent in the ortho-position(s) thereof relative to the point of attachment to the [—CH—O—] group.

In the compounds of formula (I) or (Ia), $R^1$ and $R^2$ are independently selected from substituted or unsubstituted phenyl or naphthyl. In some embodiments, $R^1$ and $R^2$ are independently selected from phenyl or naphthyl having 1 to 3 substituents. In one embodiment the substituent groups are selected from halogen and haloalkyl. In some embodiments, $R^1$ and $R^2$ are selected from mono-cyclic aromatic groups.

In some embodiments of the compounds of formula (I) or (Ia), $R^1$ and $R^2$ are independently selected from a group of formula (II):

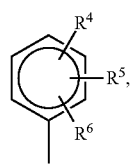

formula (II)

wherein
$R^4$, $R^5$, and $R^6$ are independently selected from hydrogen, halo, alkyl (including haloalkyl), thioalkyl, alkoxy (including haloalkoxy), alkylsulfonyl, amino, mono- and di-alkyl amino, mono- and di-aryl amino, alkylarylamino, aminoalkyl, alkylaminoalkyl, dialkylaminoalkyl, $NR^{14}C(O)R^{19}$, $NR^{14}SO_2R^{20}$, $COOR^{19}$, $OC(O)R^{20}$, $CONR^{13}R^{14}$ and $SO_2NR^{13}R^{14}$,
$R^{13}$ and $R^{14}$ are independently selected from hydrogen and alkyl or form a 5 or 6 membered ring optionally containing 1 or 2 additional heteroatoms selected from N, O, and S;
$R^{19}$ is selected from H, alkyl, aryl and heteroaryl, and
$R^{20}$ is selected from alkyl, aryl and heteroaryl.

In some embodiments of the compounds of formula (I) or (Ia), the groups $R^1$ and $R^2$ in are the same or different, and in one embodiment are different. Where $R^4$, $R^5$, and $R^6$ are selected from halo, the halo group is in some embodiments fluoro, chloro, bromo or iodo. Where $R^4$, $R^5$ and $R^6$ are selected from alkyl, thioalkyl, alkoxy and alkylsulfonyl, the alkyl is in some embodiments lower alkyl. Where $R^4$, $R^5$, and $R^6$ are selected from aminoalkyl, alkylaminoalkyl and dialkylaminoalkyl, the alkyl is selected from methyl and ethyl. Where $R^4$, $R^5$, and $R^6$ are selected from dialkylaminoalkyl, the dialkylamino fragment is in some embodiments selected from cyclicamino, such as morpholino and piperazino. Where $R^4$, $R^5$, and $R^6$ are selected from haloalkyl, the alkyl is in some embodiments methyl, and the $R^4$, $R^5$, or $R^6$ group is trifluoromethyl. Where $R^4$, $R^5$, and $R^6$ are selected from haloalkoxy, the alkyl is in some embodiments methyl and the $R^4$, $R^5$, or $R^6$ group is selected from trifluoromethoxy or difluoromethoxy. In some embodiments, one or two of $R^4$, $R^5$, and $R^6$ are hydrogen. At least one of the $R^1$ and $R^2$ groups has a non-hydrogen substituent in the ortho-position(s). The $R^1$ or $R^2$ groups in some embodiments independently have one or two non-hydrogen substituents in the ortho position(s) relative to the point of attachment to the [—CH—O—] group. Preferred ortho-substituents include halo and haloalkyl, as described herein. In some embodiments, ortho-substituents are chloro and trifluoromethyl. Where $R^{13}$ and $R^{14}$ form a 5- or 6-membered ring, the ring in some embodiments is 6-membered. Where the ring contains additional heteroatoms, in some embodiments, these are N and/or O. In some embodiments, there are 0 or 1 additional heteroatoms. In some embodiments, $R^{13}$ and $R^{14}$ are independently hydrogen or alkyl.

In some embodiments of the compounds of formula (I) or (Ia), $R^9$ is selected from hydrogen or alkyl. In some embodiments, $R^9$ is alkyl. In some embodiments, $R^9$ is selected from methyl, ethyl, propyl, sec-butyl, or tert-butyl. The alkyl group in some embodiments are substituted or unsubstituted, and in one embodiment is substituted. In some embodiments, one or two substituent groups are present. In some embodiments, substituents are hydroxy, alkoxy, thioalkyl, amino, mono- and dialkyl amino, alkoxycarbonyl, aryl, and heterocyclic groups including both heteroaryl and non-aromatic heterocyclic groups. Where $R^9$ is an acyclic alkyl group, in some embodiments it is substituted by a cyclic alkyl group; and where $R^9$ is a cyclic alkyl group in some embodiments it is substituted by an acyclic alkyl group. Where the substituent group is heteroaryl, in some embodiments the heteroaryl is a 5- or 6-membered ring containing one or more N, O, or S atoms, such as thiophenyl, furanyl, isoxazolyl, thiazolyl and benzothiophenyl. Other substituent groups in some embodiments include dihydrobenzofuranyl, dihydrobenzodioxinyl, tetrahydrofuranyl, pyrrolidinyl, oxopyrrolindyl and benzodioxolyl.

In one embodiment of a compound of formula (I), $R^3$ has the structure:

—$(CHR^9)_n(CH_2)_mCR^{10}R^{11}R^{12}$ wherein
n is 0 or 1;
m is 0, 1, 2 or 3;
$R^9$, $R^{10}$, $R^{11}$, and $R^{12}$ are selected from hydrogen, alkyl, hydroxy, alkoxy, thioalkyl, amino, mono- and di-alkyl amino, alkoxycarbonyl and $R^{13}$;
wherein $R^{13}$ is selected from aryl, heteroaryl and non-aromatic heterocyclic optionally substituted by one or more groups selected from alkyl, halogen, alkoxy, oxo, aryl, heteroaryl and non-aromatic heterocycle.

In some embodiments of Formula (I) or (Ia), m is 0 or 1 or 2. In some embodiments, m is 0 or 1. In some embodiments, n is 0. In some embodiments, n is 1 and m is 1. In one embodiment, at least one or two of $R^{10}$, $R^{11}$, and $R^{12}$ are selected from hydrogen. In a further embodiment, at least two of $R^{10}$, $R^{11}$, and $R^{12}$ are selected from methyl. In a further embodiment, $R^9$ is selected from cyclic alkyl, including cyclopentyl, cyclohexyl, norbornanyl and adamantyl. In some embodiments, $R^9$ groups are tertiary butyl, sec-butyl, isobutyl, isopropyl, n-propyl and ethyl.

In some embodiments, the CB1 antagonist of Formula (I) or (Ia) is ((R)-(+)—N-tert-butyl-3-[(4-chloro)phenyl-(2-trifluoromethyl)phenyl]methoxyazetidine-1-carboxamide (Compound ANEB-001). In some embodiments, the CB1 antagonist is ((S)-(–)—N-tert-butyl-3-[(4-chloro)phenyl-(2-trifluoromethyl)phenyl]methoxyazetidine-1-carboxamide. In some embodiments, the CB1 antagonist is (N-tert-butyl-3-[(4-chloro)phenyl-(2-trifluoromethyl)phenyl]methoxyazetidine-1-carboxamide. In some embodiments, the CB1 antagonist is Cannabigerol. In some embodiments, the CB1 antagonist is ibipinabant. In some embodiments, the CB1 antagonist is otenabant. In some embodiments, the CB1 antagonist is tetrahydrocannabivarin. In some embodiments, the CB1 antagonist is virodhamine. In some embodiments, the CB1 inverse agonist is rimonabant. In some embodiments, the CB1 inverse agonist is taranabant. In some embodiments, the CB1 inverse agonist is surinabant or drinabant. In some embodiments, a composition or formulation described herein comprises two or more CB1 inhibitors. In some embodiments, the CB1 inhibitor is a neutral antagonist. In some instances, the CB1 inhibitors comprise one or more substitutions at the phenyl groups that function as effective neutral antagonists of CB1.

In some instances, a CB1 inhibitor comprises a structure of formula (Ia), wherein $R^1$ and $R^2$ are substituted aromatic groups, and $R^3$ is an optionally substituted $C_1$-$C_6$ alkyl group. In some instances, $R^3$ is tert-butyl. In some instances, $R^3$ is isopropyl. In some instances, $R^3$ is sec-butyl. In some instances, le is a substituted aromatic group. In some instances, le is an optionally substituted phenyl group. In some instances, le is a phenyl group substituted with a halogen (e.g., F, Cl, Br, I). In some instances, le is a phenyl group substituted with Cl. In some instances, le is a phenyl group para substituted in (4-position) with a halogen (e.g., F, Cl, Br, I). In some instances, le is a 4-chlorophenyl group. In some instances, $R^2$ is a substituted aromatic group. In some instances, $R^2$ is an optionally substituted phenyl group. In some instances, $R^2$ is a phenyl group substituted with a $C_1$-$C_5$ alkyl group. In some instances, $R^2$ is a phenyl group substituted with a $C_1$-$C_5$ trifluoroalkyl group. In some instances, $R^2$ is a phenyl group substituted with a trifluoromethyl group. In some instances, $R^2$ is a phenyl group ortho substituted in (4-position) with a $C_1$-$C_5$ trifluoroalkyl group. In some instances, $R^2$ is a 2-trifluoromethylphenyl group. In some embodiments, the CB1 inhibitor is compound ANEB-001, having the following structure:

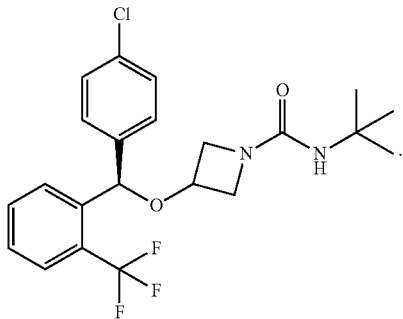 [SMILES: CC(C)(C)NC(=O)N1CC(O[C@H](c2ccc(Cl)cc2)c2ccccc2C(F)(F)F)C1]

Methods of producing ANEB-001 and related compounds (and enantiomers thereof) are known in the art (see Example 81 of U.S. Pat. No. 7,504,522 which is incorporated by reference). In some embodiments, the CB1 inhibitor has the structure:

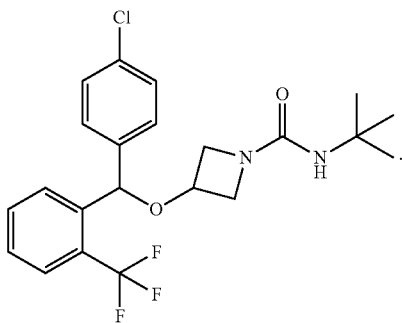 [SMILES: CC(C)(C)NC(=O)N1CC(OC(c2ccc(Cl)cc2)c2ccccc2C(F)(F)F)C1]

In some embodiments, the CB1 inhibitor has the structure:

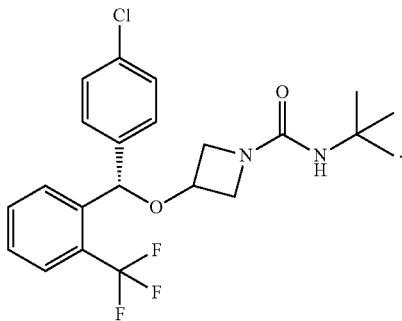 [SMILES: CC(C)(C)NC(=O)N1CC(O[C@@H](c2ccc(Cl)cc2)c2ccccc2C(F)(F)F)C1]

In some embodiments, a CB1 inhibitor is a compound of Table 1.

TABLE 1

| # | Name | Structure |
|---|------|-----------|
| 1 | 3-[(R)-2-(trifluoromethyl)-4'-chlorobenzhydryloxy]-N-(tert-butyl)azetidine-1-carboxamide (ANEB-001) | 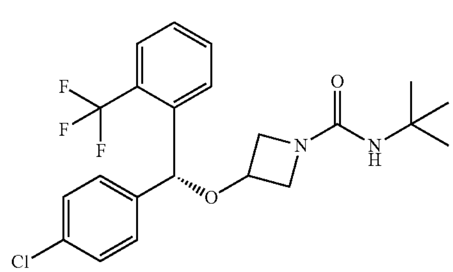 [SMILES: CC(C)(C)NC(=O)N1CC(O[C@H](c2ccc(Cl)cc2)c2ccccc2C(F)(F)F)C1] |

TABLE 1-continued

| # | Name | Structure |
|---|------|-----------|
| 2 | 3-(2,4,4'-trichlorobenzhydryloxy)-N-(tert-butyl)azetidine-1-carboxamide | 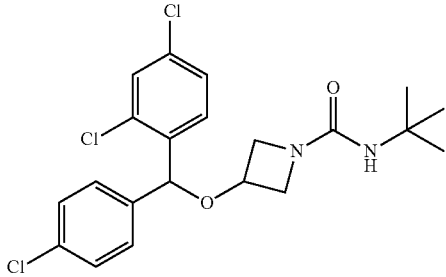 [SMILES: CC(C)(C)NC(=O)N1CC(OC(c2ccc(Cl)cc2)c2ccc(Cl)cc2Cl)C1] |
| 3 | 3-(2,4'-dichlorobenzhydryloxy)-N-(ethyl propionate-2-yl)azetidine-1-carboxamide | 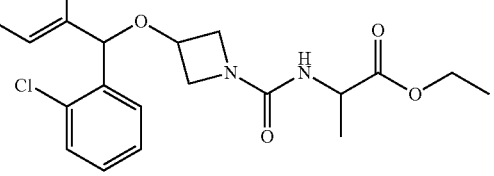 |
| 4 | 3-(2,4'-dichlorobenzhydryloxy)-N-(tert-butyl)azetidine-1-carboxamide | 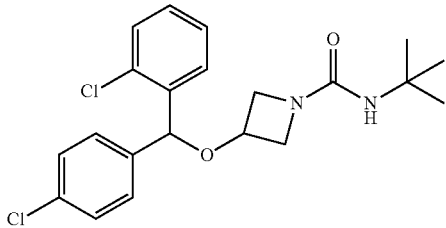 [SMILES: CC(C)(C)NC(=O)N1CC(OC(c2ccc(Cl)cc2)c2ccccc2Cl)C1] |
| 5 | 3-(2,4'-dichlorobenzhychyloxy)-N-(2-thiophen-2-yl ethyl)azetidine-1-carboxamide | 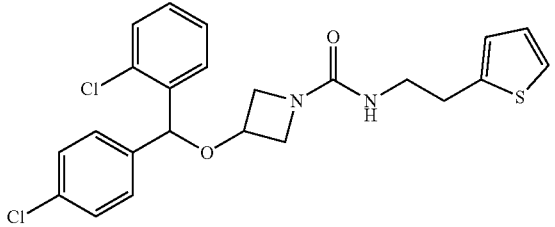 [SMILES: O=C(NCCc1cccs1)N1CC(OC(c2ccc(Cl)cc2)c2ccccc2Cl)C1] |
| 6 | 3-(2,4'-dichlorobenzhydryloxy)-N-[ethyl 4-(methylthio)butyrate-2-yl]azetidine-1-carboxamide | 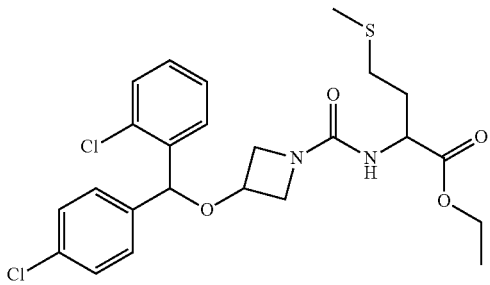 [SMILES: CCOC(=O)C(CCSC)NC(=O)N1CC(OC(c2ccc(Cl)cc2)c2ccccc2Cl)C1] |
| 7 | 3-(2,4'-dichlorobenzhydryloxy)-N-(cyclopropylmethyl)azetidine-1-carboxamide | 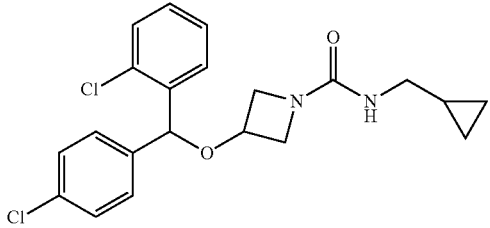 [SMILES: O=C(NCC1CC1)N1CC(OC(c2ccc(Cl)cc2)c2ccccc2Cl)C1] |

TABLE 1-continued

| # | Name | Structure |
|---|------|-----------|
| 8 | 3-(2,4'-dichlorobenzhychyloxy)-N-(2,3-dihydrobenzofuran-5-yl-methyl)azetidine-1-carboxamide | 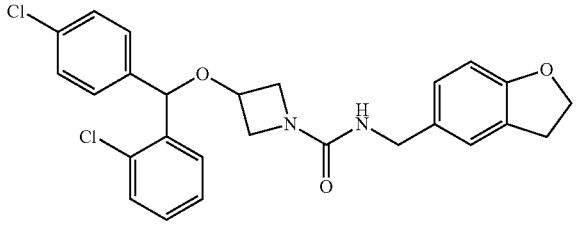 [SMILES: O=C(NCc1ccc2c(c1)CCO2)N1CC(OC(c2ccc(Cl)cc2)c2ccccc2Cl)C1] |
| 9 | 3-(2,4'-dichlorobenzhychyloxy)-N-(2,5-dimethylfuran-3-yl-methyl)azetidine-1-calboxamide | 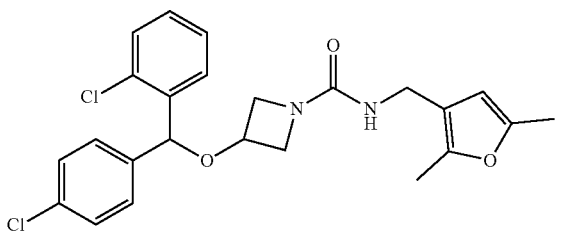 [SMILES: Cc1cc(CNC(=O)N2CC(OC(c3ccc(Cl)cc3)c3ccccc3Cl)C2)c(C)o1] |
| 10 | 3-(2,4'-dichlorobenzhychyloxy)-N-(2,3-Dihydro-benzo[1,4]dioxin-2-yl-methyl)azetidine-1-carboxamide | 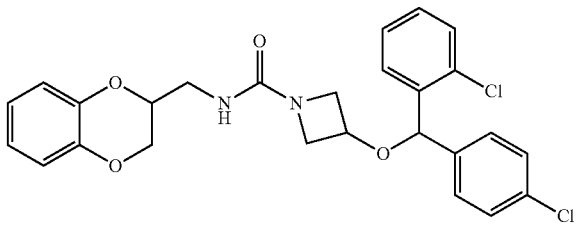 [SMILES: O=C(NCC1COc2ccccc2O1)N1CC(OC(c2ccc(Cl)cc2)c2ccccc2Cl)C1] |
| 11 | 3-(2,4'-dichlorobenzhydryloxy)-N-(5-methyl-isoxazol-3-yl-methyl)azetidine-1-carboxamide | 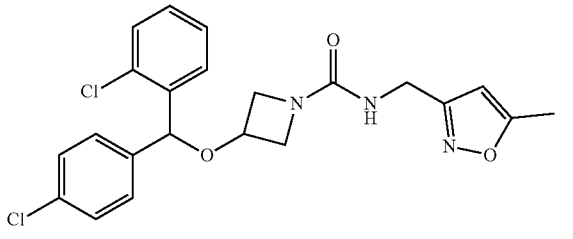 [SMILES: Cc1cc(CNC(=O)N2CC(OC(c3ccc(Cl)cc3)c3ccccc3Cl)C2)no1] |
| 12 | 3-(2,4'-dichlorobenzhydryloxy)-N-[(R)-sec-butyl]azetidine-1-carboxamide | 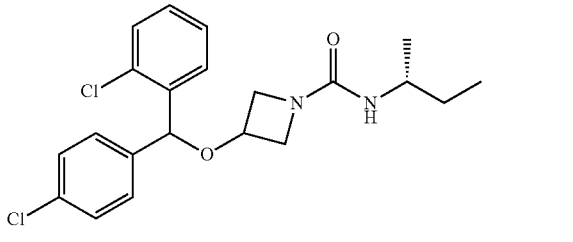 [SMILES: CC[C@@H](C)NC(=O)N1CC(OC(c2ccc(Cl)cc2)c2ccccc2Cl)C1] |
| 13 | 3-(2,4'-dichlorobenzhydryloxy)-N-(2-bromothiophen-3-yl-methyl)azetidine-1-carboxamide | 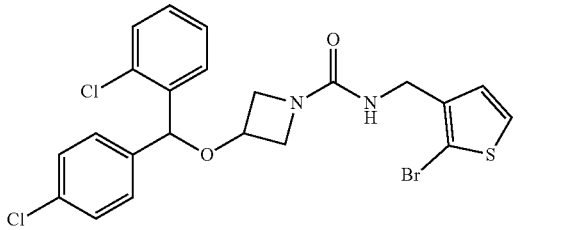 [SMILES: O=C(NCc1ccsc1Br)N1CC(OC(c2ccc(Cl)cc2)c2ccccc2Cl)C1] |

TABLE 1-continued

| # | Name | Structure |
|---|------|-----------|
| 14 | 3-(2,4'-dichlorobenzhydryloxy)-N-[(S)-sec-butyl]azetidine-1-carboxamide | 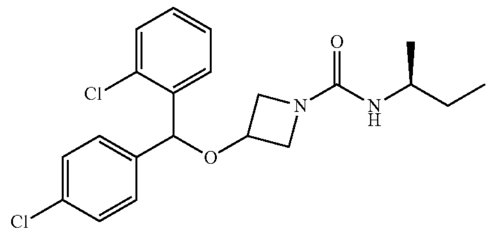 [SMILES: CC[C@H](C)NC(=O)N1CC(OC(c2ccc(Cl)cc2)c2ccccc2Cl)C1] |
| 15 | 3-(2,4'-dichlorobenzhydryloxy)-N-(thiophen-3-yl-methyl)azetidine-1-carboxamide | 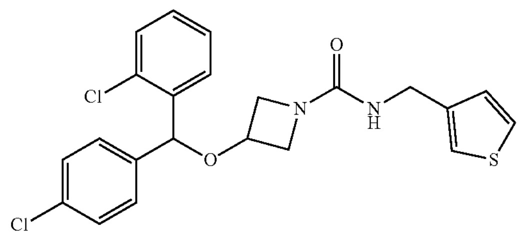 [SMILES: O=C(NCc1ccsc1)N1CC(OC(c2ccc(Cl)cc2)c2ccccc2Cl)C1] |
| 16 | 3-(2,4'-dichlorobenzhydryloxy)-N-(2 methoxyphenylmethyl)azetidine-1-carboxamide | 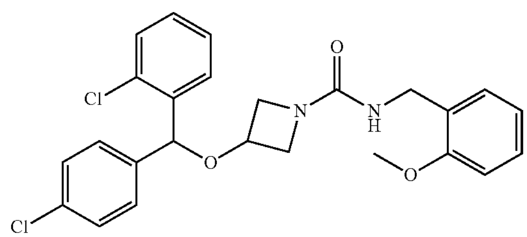 [SMILES: COc1ccccc1CNC(=O)N1CC(OC(c2ccc(Cl)cc2)c2ccccc2Cl)C1] |
| 17 | 3-(2,4'-dichlorobenzhydryloxy)-N-(2-furanylmethyl)azetidine-1-carboxamide | 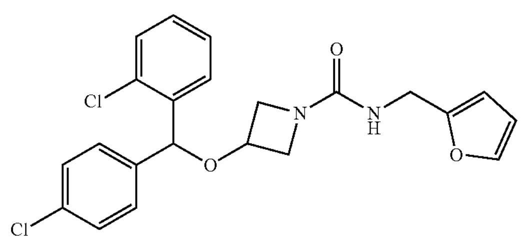 [SMILES: O=C(NCc1ccco1)N1CC(OC(c2ccc(Cl)cc2)c2ccccc2Cl)C1] |
| 18 | 3-(2,4'-dichlorobenzhydryloxy)-N-(3-ethoxypropyl)azetidine-1-carboxamide | 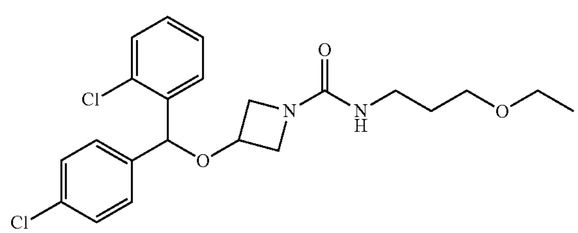 [SMILES: CCOCCCNC(=O)N1CC(OC(c2ccc(Cl)cc2)c2ccccc2Cl)C1] |
| 19 | 3-(2,4'-dichlorobenzhydryloxy)-N-(2-tetrahydrofuranylmethyl)azetidine-1-carboxamide | 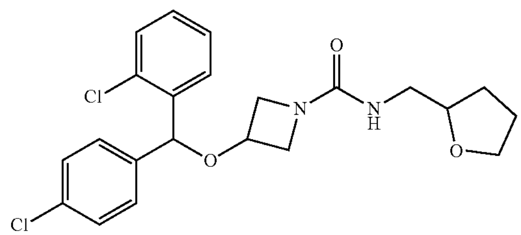 [SMILES: O=C(NCC1CCCO1)N1CC(OC(c2ccc(Cl)cc2)c2ccccc2Cl)C1] |

TABLE 1-continued

| # | Name | Structure |
|---|------|-----------|
| 20 | 3-(2,4'-dichlorobenzhydryloxy)-N-(exo-2-norbornanyl)azetidine-1-carboxamide | 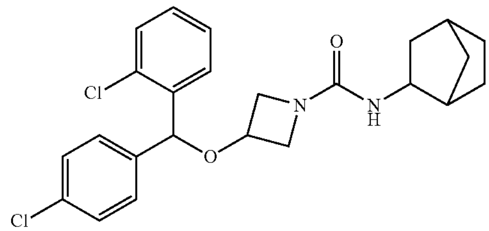 [SMILES: O=C(NC1CC2CCC1C2)N1CC(OC(c2ccc(Cl)cc2)c2ccccc2Cl)C1] |
| 21 | 3-(2,4'-dichlorobenzhydryloxy)-N-(1-phenylpropyl)azetidine-1-carboxamide | 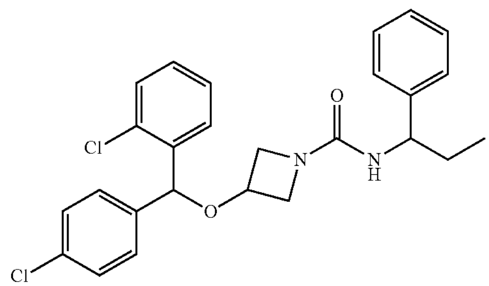 [SMILES: CCC(NC(=O)N1CC(OC(c2ccc(Cl)cc2)c2ccccc2Cl)C1)c1ccccc1] |
| 22 | 3-(2,4'-dichlorobenzhydryloxy)-N-[(R)-a-methylbenzyl]azetidine-1-carboxamide | 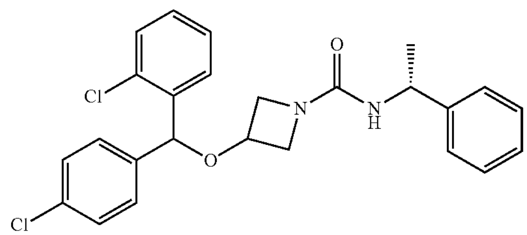 [SMILES: C[C@@H](NC(=O)N1CC(OC(c2ccc(Cl)cc2)c2ccccc2Cl)C1)c1ccccc1] |
| 23 | 3-(2,4'-dichlorobenzhythyloxy)-N-[(R)-1-(3-methoxyphenyl)ethyl]azetidine-1-calboxamide | 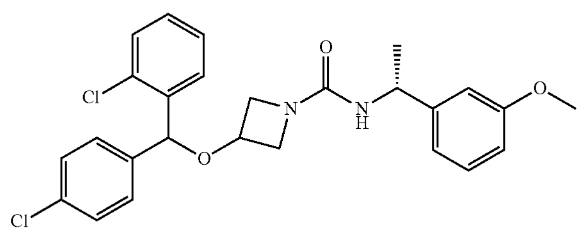 [SMILES: COc1cccc([C@@H](C)NC(=O)N2CC(OC(c3ccc(Cl)cc3)c3ccccc3Cl)C2)c1] |
| 24 | 3-(2,4'-dichlorobenzhythyloxy)-N-[(S)-1-(3-methoxyphenyl)ethyl]azetidine-1-carboxamide | 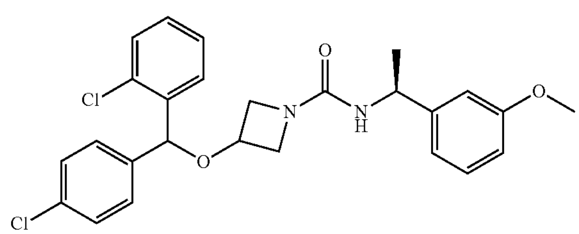 [SMILES: COc1cccc([C@H](C)NC(=O)N2CC(OC(c3ccc(Cl)cc3)c3ccccc3Cl)C2)c1] |
| 25 | 3-(4,4'-dichlorobenzhydryloxy)-N-(1-adamantyl)azetidine-1-carboxamide | 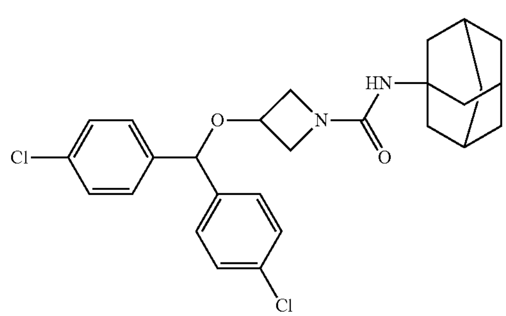 [SMILES: O=C(NC12CC3CC(CC(C3)C1)C2)N1CC(OC(c2ccc(Cl)cc2)c2ccc(Cl)cc2)C1] |

TABLE 1-continued

| # | Name | Structure |
|---|------|-----------|
| 26 | 3-(4,4'-dichlorobenzhydryloxy)-N-(benzo[b]thiophen-2-yl-methyl)azetidine-1-carboxamide | 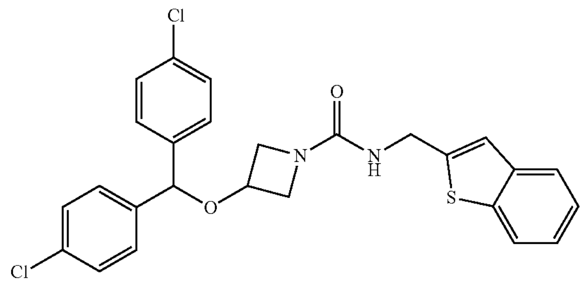 [SMILES: O=C(NCc1cc2ccccc2s1)N1CC(OC(c2ccc(Cl)cc2)c2ccc(Cl)cc2)C1] |
| 27 | 3-(2,2'-dichlorobenzhydryloxy)-N-(1-adamantyl)azetidine-1-carboxamide | 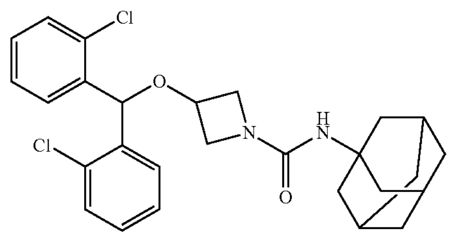 [SMILES: O=C(NC12CC3CC(CC(C3)C1)C2)N1CC(OC(c2ccccc2Cl)c2ccccc2Cl)C1] |
| 28 | 3-(4,4'-dibromobenzhydryloxy)-N-(tert-butyl)azetidine-1-carboxamide | 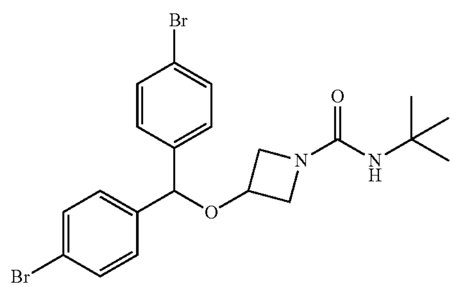 [SMILES: CC(C)(C)NC(=O)N1CC(OC(c2ccc(Br)cc2)c2ccc(Br)cc2)C1] |
| 29 | 3-(4,4'-dibromobenzhydryloxy)-N-(1-adamantyl)azetidine-1-carboxamide | 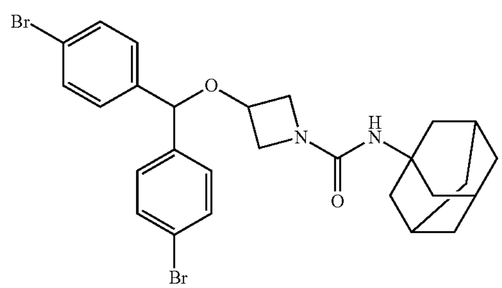 [SMILES: O=C(NC12CC3CC(CC(C3)C1)C2)N1CC(OC(c2ccc(Br)cc2)c2ccc(Br)cc2)C1] |
| 30 | 3-[2-(trifluoromethyl)-4'-chlorobenzhydryloxy]-N-(tert-butyl)azetidine-1-carboxamide | 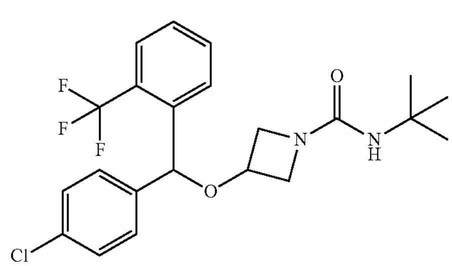 [SMILES: CC(C)(C)NC(=O)N1CC(OC(c2ccc(Cl)cc2)c2ccccc2C(F)(F)F)C1] |

TABLE 1-continued

| # | Name | Structure |
|---|------|-----------|
| 31 | 3-[2-(trifluoromethyl)-4'-chlorobenzhydryloxy]-N-(n-propyl)azetidine-1-carboxamide | 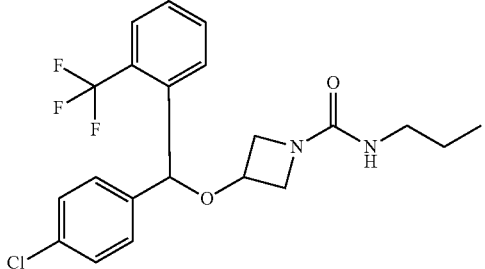 [SMILES: CCCNC(=O)N1CC(OC(c2ccc(Cl)cc2)c2ccccc2C(F)(F)F)C1] |
| 32 | 3-[2-(trifluoromethyl)-4'-chlorobenzhydryloxy]-N-(iso-propyl)azetidine-1-carboxamide | 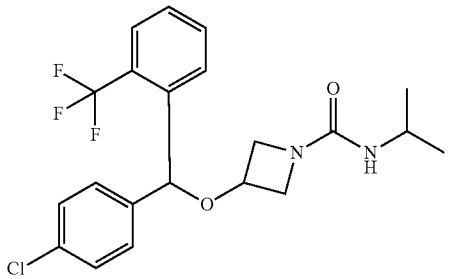 [SMILES: CC(C)NC(=O)N1CC(OC(c2ccc(Cl)cc2)c2ccccc2C(F)(F)F)C1] |
| 33 | 3-[2-(trifluoromethyl)-4'-chlorobenzhydryloxy]-N-(n-butyl)azetidine-1-carboxamide | 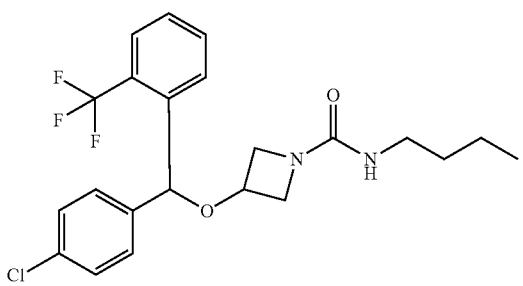 [SMILES: CCCCNC(=O)N1CC(OC(c2ccc(Cl)cc2)c2ccccc2C(F)(F)F)C1] |
| 34 | 3-[2-(trifluoromethyl)-4'-chlorobenzhydryloxy]-N-(sec-butyl)azetidine-1 carboxamide | 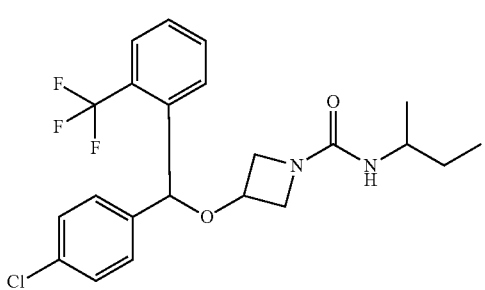 [SMILES: CCC(C)NC(=O)N1CC(OC(c2ccc(Cl)cc2)c2ccccc2C(F)(F)F)C1] |
| 35 | 3-[2-(trifluoromethyl)-4'-chlorobenzhydryloxy]-N-(ethylpropionate-3-yl)azetidine-1-carboxamide | 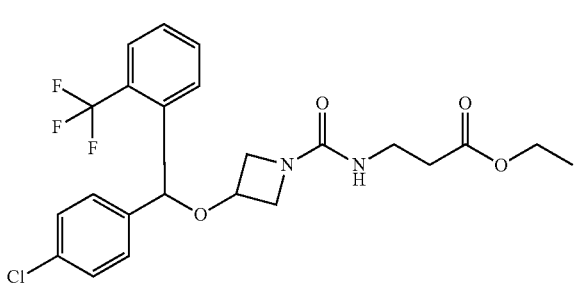 [SMILES: CCOC(=O)CCNC(=O)N1CC(OC(c2ccc(Cl)cc2)c2ccccc2C(F)(F)F)C1] |

TABLE 1-continued

| # | Name | Structure |
|---|------|-----------|
| 36 | 3-[2-(trifluoromethyl)-4'-chlorobenzhydryloxy]-N-(ethyl 3-phenylpropionate-2-yl)azetidine-1-carboxamide | 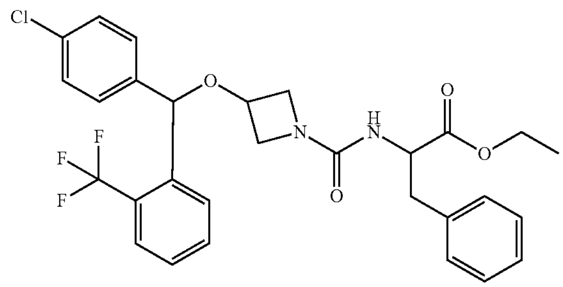 [SMILES: CCOC(=O)C(Cc1ccccc1)NC(=O)N1CC(OC(c2ccc(Cl)cc2)c2ccccc2C(F)(F)F)C1] |
| 37 | 3-[2-(trifluoromethyl)-4'-chlorobenzhydryloxy]-N-(ethyl)azetidine-1-carboxamide | 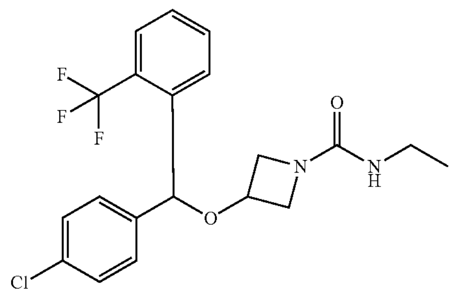 [SMILES: CCNC(=O)N1CC(OC(c2ccc(Cl)cc2)c2ccccc2C(F)(F)F)C1] |
| 38 | 3-[2-(trifluoromethyl)-4'-chlorobenzhydryloxy]-N-[(S)-a-methyl-benzyl]azetidine-1-carboxamide | 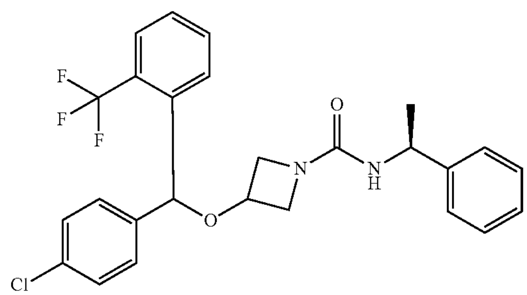 [SMILES: C[C@H](NC(=O)N1CC(OC(c2ccc(Cl)cc2)c2ccccc2C(F)(F)F)C1)c1ccccc1] |
| 39 | 3-[2-(trifluoromethyl)-4'-chlorobenzhydryloxy]-N-(2,2,4-trimethylpent-4-yl)azetidine-1-carboxamide | 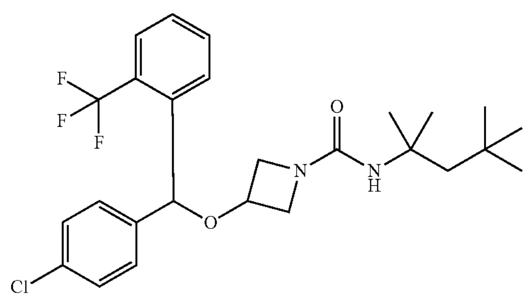 [SMILES: CC(C)(C)CC(C)(C)NC(=O)N1CC(OC(c2ccc(Cl)cc2)c2ccccc2C(F)(F)F)C1] |
| 40 | 3-[2-(trifluoromethyl)-4'-chlorobenzhydryloxy]-N-(cyclopentyl)azetidine-1-carboxamide | 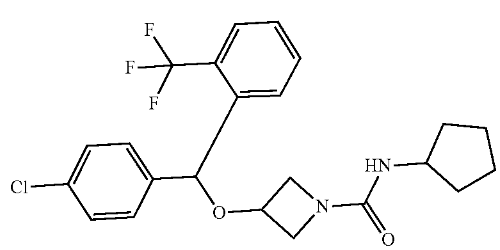 [SMILES: O=C(NC1CCCC1)N1CC(OC(c2ccc(Cl)cc2)c2ccccc2C(F)(F)F)C1] |

TABLE 1-continued

| # | Name | Structure |
|---|------|-----------|
| 41 | 3-(2,4'-dichlorobenzhychyloxy)-N-(2,2,4-trimethylpent-4-yl)azetidine-1-carboxamide | 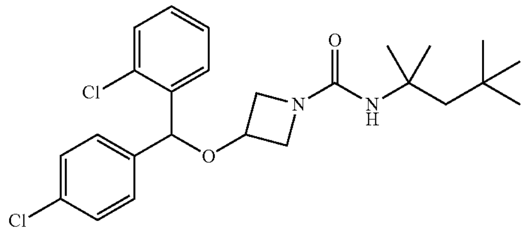 [SMILES: CC(C)(C)CC(C)(C)NC(=O)N1CC(OC(c2ccc(Cl)cc2)c2ccccc2Cl)C1] |
| 42 | 3-(2,4'-dichlorobenzhydryloxy)-N-(2-methylbut-2-yl)azetidine-1-carboxamide | 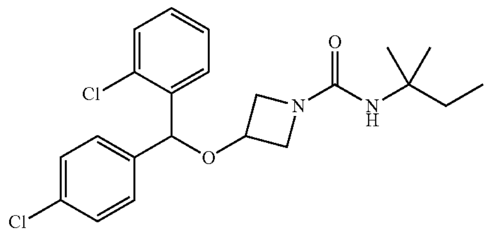 [SMILES: CCC(C)(C)NC(=O)N1CC(OC(c2ccc(Cl)cc2)c2ccccc2Cl)C1] |
| 43 | 3-[2-(trifluoromethyl)-2'-fluoro-4'-bromobenzhydryloxy]-N-(tert-butyl)azetidine-carboxamide | 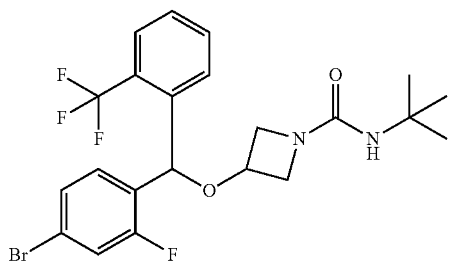 [SMILES: CC(C)(C)NC(=O)N1CC(OC(c2ccc(Br)cc2F)c2ccccc2C(F)(F)F)C1] |
| 44 | 3-[2-(trifluoromethyl)-4'-(methylthio)benzhydryloxy]-N-(tert-butyl)azetidine-1-calboxamide | 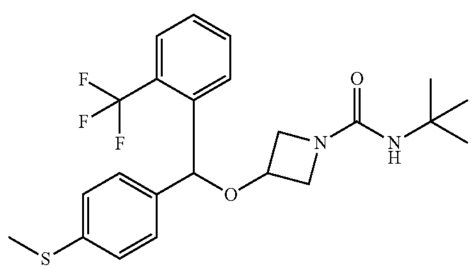 [SMILES: CSc1ccc(C(OC2CN(C(=O)NC(C)(C)C)C2)c2ccccc2C(F)(F)F)cc1] |
| 45 | 3-[2-(trifluoromethyl)-4'-(methylthio)benzhydryloxy]-N-(iso-propyl)azetidine-1-carboxamide | 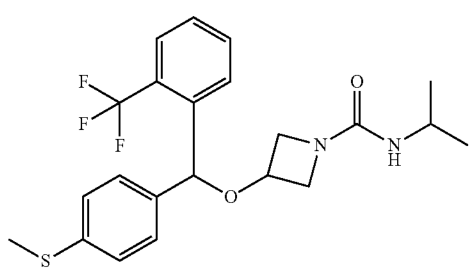 [SMILES: CSc1ccc(C(OC2CN(C(=O)NC(C)C)C2)c2ccccc2C(F)(F)F)cc1] |
| 46 | 3-[2-(trifluoromethyl)-4'-(methylthio)benzhydryloxy]-N-(sec-butyl)azetidine-1-carboxamide | 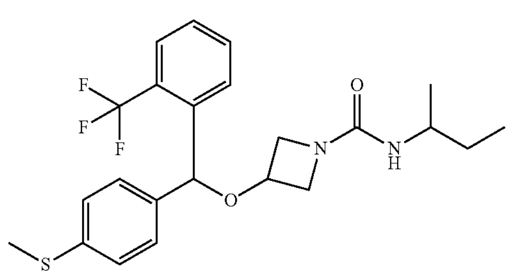 [SMILES: CCC(C)NC(=O)N1CC(OC(c2ccc(SC)cc2)c2ccccc2C(F)(F)F)C1] |

TABLE 1-continued

| # | Name | Structure |
|---|------|-----------|
| 47 | 3-[2-(trifluoromethyl)-4'-(methylthio)benzhydryloxy]-N-(benzyl)azetidine-1-carboxamide | 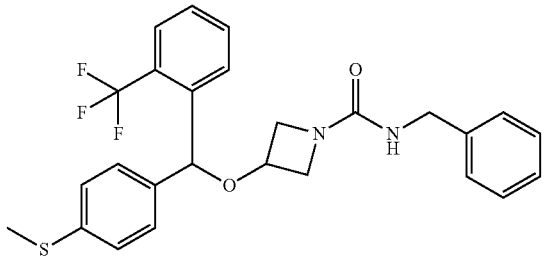 [SMILES: CSc1ccc(C(OC2CN(C(=O)NCc3ccccc3)C2)c2ccccc2C(F)(F)F)cc1] |
| 48 | 3-[2-(trifluoromethyl)-4-fluoro-4'-chlorobenzhydryloxy]-N-(tert-butyl)azetidine-1-carboxamide | 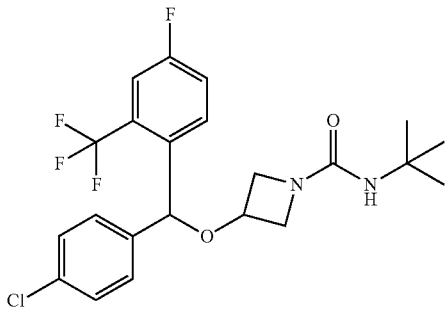 [SMILES: CC(C)(C)NC(=O)N1CC(OC(c2ccc(Cl)cc2)c2ccc(F)cc2C(F)(F)F)C1] |
| 49 | 3-[2-(trifluoromethyl)-4-fluoro-4'-chlorobenzhydryloxy]-N-(iso-propyl)azetidine-carboxamide | 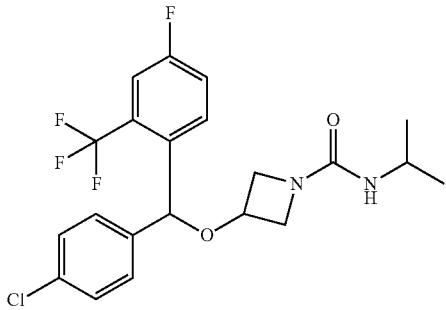 [SMILES: CC(C)NC(=O)N1CC(OC(c2ccc(Cl)cc2)c2ccc(F)cc2C(F)(F)F)C1] |
| 50 | 3-[2-(trifluoromethyl)-4-fluoro-4'-chlorobenzhydryloxy]-N-(sec-butyl)azetidine-1-carboxamide | 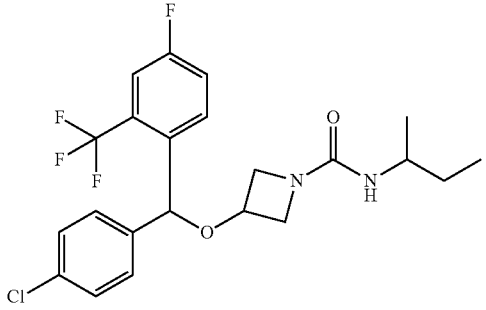 [SMILES: CCC(C)NC(=O)N1CC(OC(c2ccc(Cl)cc2)c2ccc(F)cc2C(F)(F)F)C1] |
| 51 | 3-[2-(trifluoromethyl)-4-fluoro-4'-chlorobenzhydryloxy]-N-(cyclohexyl)azetidine-1-carboxamide | 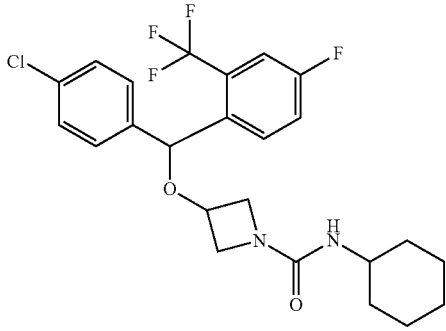 [SMILES: O=C(NC1CCCCC1)N1CC(OC(c2ccc(Cl)cc2)c2ccc(F)cc2C(F)(F)F)C1] |

TABLE 1-continued

| # | Name | Structure |
|---|------|-----------|
| 52 | 3-[2-(trifluoromethyl)-4-fluoro-4'-chlorobenzhydryloxy]-N-(benzyl)azetidine-1-carboxamide | 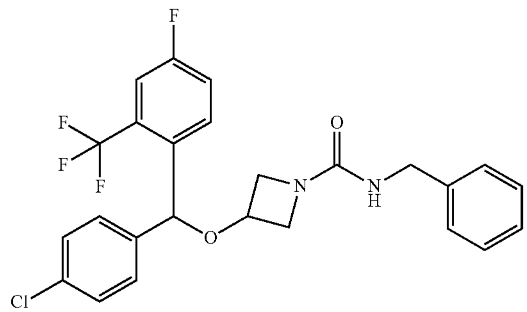 [SMILES: O=C(NCc1ccccc1)N1CC(OC(c2ccc(Cl)cc2)c2ccc(F)cc2C(F)(F)F)C1] |
| 53 | 3-[2-(trifluoromethyl)benzhydryloxy]-N-(tert-butyl)azetidine-1-carboxamide | 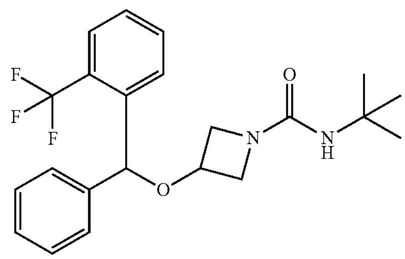 [SMILES: CC(C)(C)NC(=O)N1CC(OC(c2ccccc2)c2ccccc2C(F)(F)F)C1] |
| 54 | 3-[2(trifluoromethyl)benzhydryloxy]-N-(iso-propyl)azetidine-1-carboxamide | 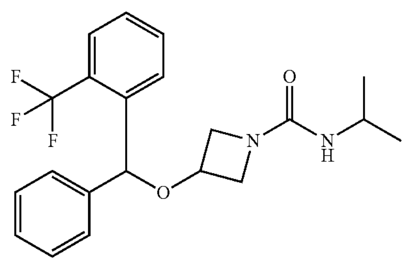 [SMILES: CC(C)NC(=O)N1CC(OC(c2ccccc2)c2ccccc2C(F)(F)F)C1] |
| 55 | 3-[2(trifluoromethyl)benzhydryloxy]-N-(sec-butyl)azetidine-1-carboxamide | 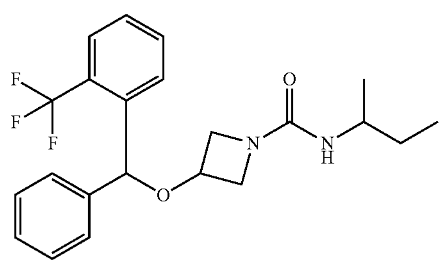 [SMILES: CCC(C)NC(=O)N1CC(OC(c2ccccc2)c2ccccc2C(F)(F)F)C1] |
| 56 | 3-[2(trifluoromethyl)benzhydryloxy]-N-(cyclohexyl)azetidine-1-carboxamide | 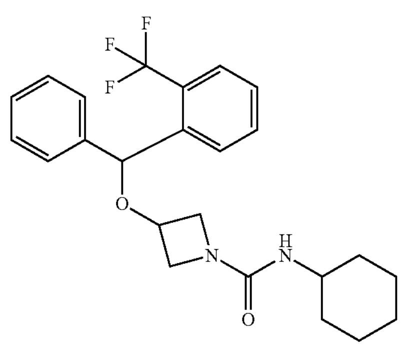 [SMILES: O=C(NC1CCCCC1)N1CC(OC(c2ccccc2)c2ccccc2C(F)(F)F)C1] |

TABLE 1-continued

| # | Name | Structure |
|---|------|-----------|
| 57 | 3-[2(trifluoromethyl)benzhydryloxy]-N-(benzyl)azetidine-1-carboxamide | 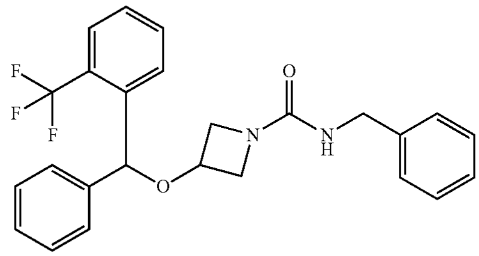 [SMILES: O=C(NCc1ccccc1)N1CC(OC(c2ccccc2)c2ccccc2C(F)(F)F)C1] |
| 58 | N-(tert-butyl)-3-((4-(trifluoromethoxy)phenyl)(2-(trifluoromethyl)phenyl)methoxy)azetidine-1-carboxamide | 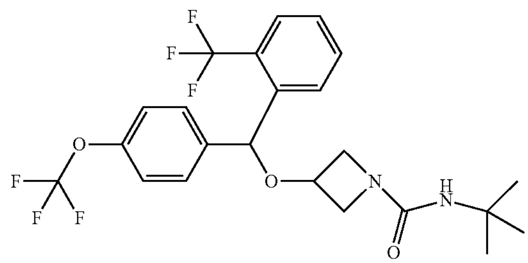 [SMILES: CC(C)(C)NC(=O)N1CC(OC(c2ccc(OC(F)(F)F)cc2)c2ccccc2C(F)(F)F)C1] |
| 59 | 3-[2-(trifluoromethyl)-4'-(trifluoromethoxy)benzhydryloxy]-N-(iso-propyl)azetidine-1-carboxamide | 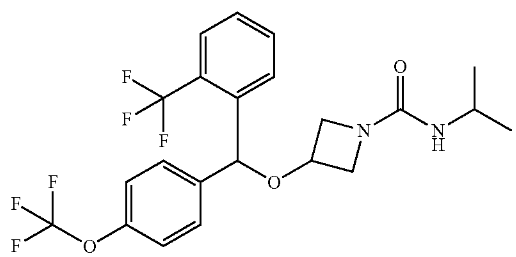 [SMILES: CC(C)NC(=O)N1CC(OC(c2ccc(OC(F)(F)F)cc2)c2ccccc2C(F)(F)F)C1] |
| 60 | 3-[2-(trifluoromethyl)-4'-(trifluoromethoxy)benzhydryloxy]-N-(sec-butyl)azetidine-1-carboxamide | 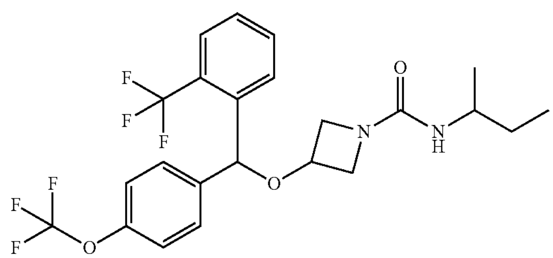 [SMILES: CCC(C)NC(=O)N1CC(OC(c2ccc(OC(F)(F)F)cc2)c2ccccc2C(F)(F)F)C1] |
| 61 | 3-[2-(trifluoromethyl)-4'-(trifluoromethoxy)benzhydryloxy]-N-(benzyl)azetidine-1-carboxamide | 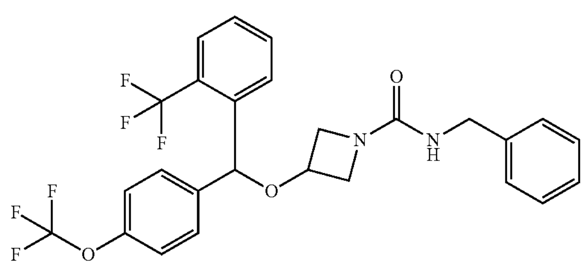 [SMILES: O=C(NCc1ccccc1)N1CC(OC(c2ccc(OC(F)(F)F)cc2)c2ccccc2C(F)(F)F)C1] |
| 62 | 3-[2-(trifluoromethyl)-4'-chlorobenzhydryloxy]-N-(1-adamantyl)azetidine-1-carboxamide | 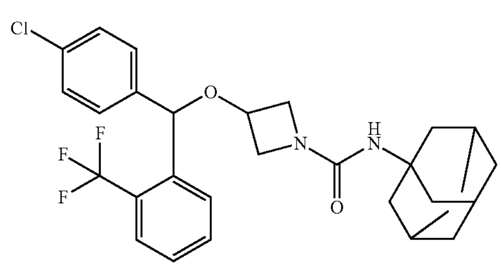 [SMILES: CC1CC2CC(C)CC(NC(=O)N3CC(OC(c4ccc(Cl)cc4)c4ccccc4C(F)(F)F)C3)(C1)C2] |

TABLE 1-continued

| # | Name | Structure |
|---|------|-----------|
| 63 | 3-[2-(trifluoromethyl)-4'-chlorobenzhydryloxy]-N-(cyclohexyl)azetidine-1-carboxamide | 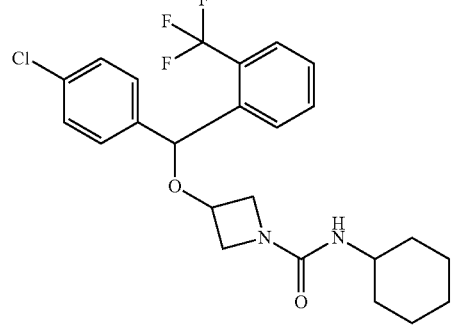 |
| 64 | 3-[2-(trifluoromethyl)-4'-chlorobenzhydryloxy]-N-(tert-amyl)azetidine-1-carboxamide | 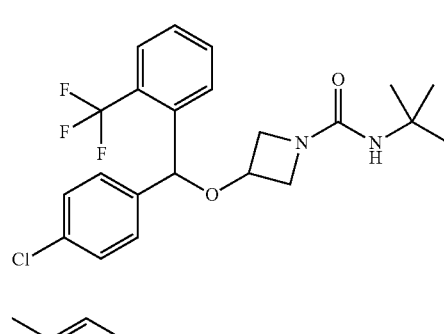 |
| 65 | 3-[2-(trifluoromethyl)-4'-methylbenzhydryloxy]-N-(1-adamantyl)azetidine-1-carboxamide | 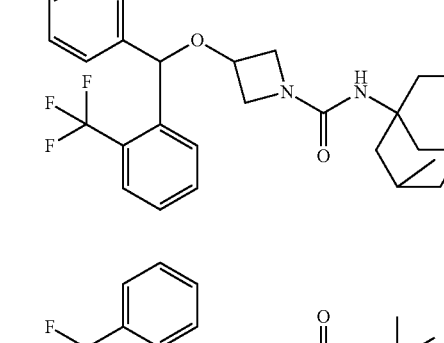 |
| 66 | 3-[2-(trifluoromethyl)-4'-methylbenzhydryloxy]-N-(tert-butyl)azetidine-1-carboxamide | 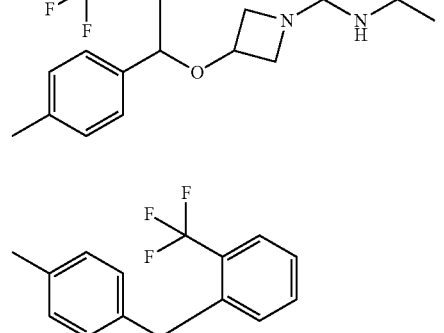 |
| 67 | 3-[2-(trifluoromethyl)-4'-methylbenzhydryloxy]-N-(cyclohexyl)azetidine-1-carboxamide | 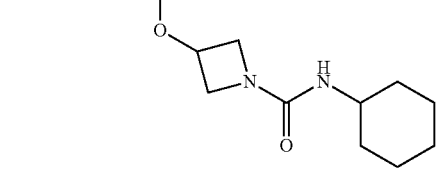 |

TABLE 1-continued

| # | Name | Structure |
|---|------|-----------|
| 68 | 3-[2-(trifluoromethyl)-4'-methoxybenzhydryloxy]-N-(1-adamantyl)azetidine-1-carboxamide | 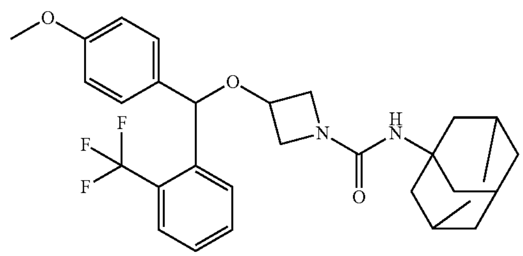 [SMILES: COc1ccc(C(OC2CN(C(=O)NC34CC(C)CC(CC(C)C3)C4)C2)c2ccccc2C(F)(F)F)cc1] |
| 69 | 3-[2-(trifluoromethyl)-4'-methoxybenzhythyloxy]-N-(tert-butyl)azetidine-1-carboxamide | 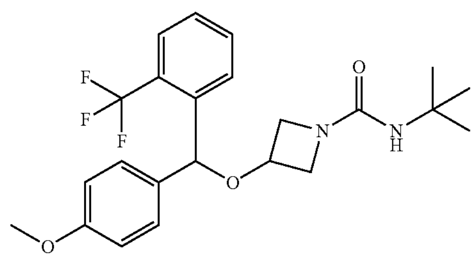 [SMILES: COc1ccc(C(OC2CN(C(=O)NC(C)(C)C)C2)c2ccccc2C(F)(F)F)cc1] |
| 70 | 3-[2-(trifluoromethyl)-4'-fluorobenzhydryloxy]-N-(1-adamantyl)azetidine-1-carboxamide | 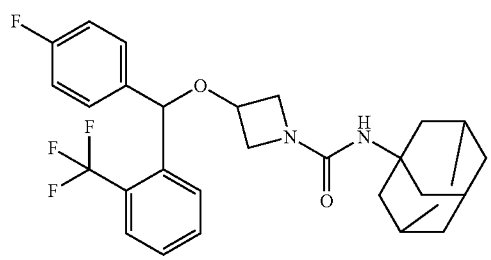 [SMILES: CC1CC2CC(C)CC(NC(=O)N3CC(OC(c4ccc(F)cc4)c4ccccc4C(F)(F)F)C3)(C1)C2] |
| 71 | 3-[2-(trifluoromethyl)-4'-fluorobenzhydryloxy]-N-(tert-butyl)azetidine-1-carboxamide | 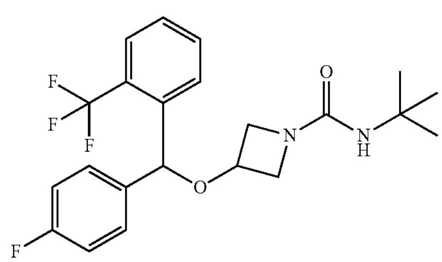 [SMILES: CC(C)(C)NC(=O)N1CC(OC(c2ccc(F)cc2)c2ccccc2C(F)(F)F)C1] |
| 72 | 3-[2-(trifluoromethyl)-4'-fluorobenzhydryloxy]-N-(cyclohexyl)azetidine-1-carboxamide | 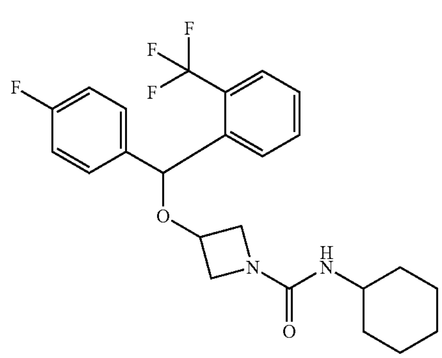 [SMILES: O=C(NC1CCCCC1)N1CC(OC(c2ccc(F)cc2)c2ccccc2C(F)(F)F)C1] |

TABLE 1-continued

| # | Name | Structure |
|---|------|-----------|
| 73 | 3-[2-(trifluoromethyl)-4'-chlorobenzhydryloxy]-N-(allyl)azetidine-1-carboxamide | 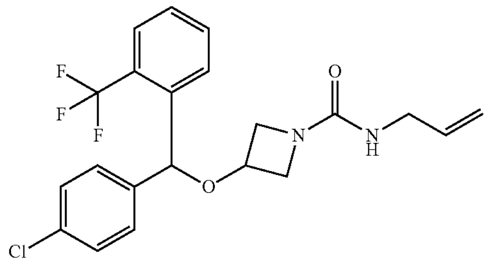 [SMILES: C=CCNC(=O)N1CC(OC(c2ccc(Cl)cc2)c2ccccc2C(F)(F)F)C1] |
| 74 | 3-[2-(trifluoromethyl)-4'-(methylthio)benzhydryloxy]-N-(1-adamantyl)azetidine-1-carboxamide | 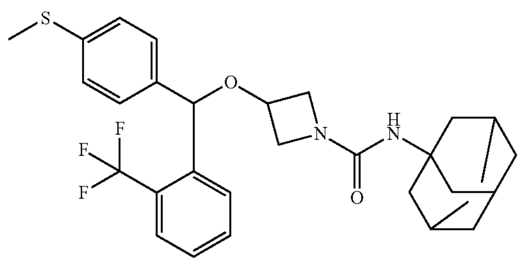 [SMILES: CSc1ccc(C(OC2CN(C(=O)NC34CC(C)CC(CC(C)C3)C4)C2)c2ccccc2C(F)(F)F)cc1] |
| 75 | 3-[2-(trifluoromethyl)-4'-(methylthio)benzhydryloxy]-N-(cyclohexyl)azetidine-1-carboxamide | 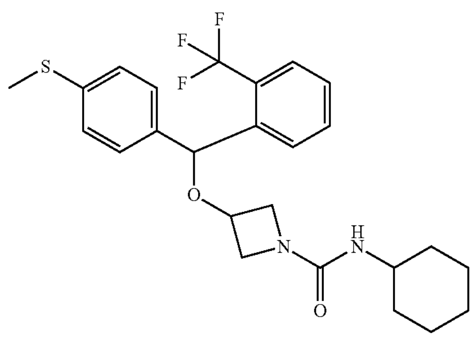 [SMILES: CSc1ccc(C(OC2CN(C(=O)NC3CCCCC3)C2)c2ccccc2C(F)(F)F)cc1] |
| 76 | N-(tert-butyl)-3-((4-(difluoromethoxy)phenyl)(2-(trifluoromethyl)phenypmethoxy)azetidine-1-carboxamide | 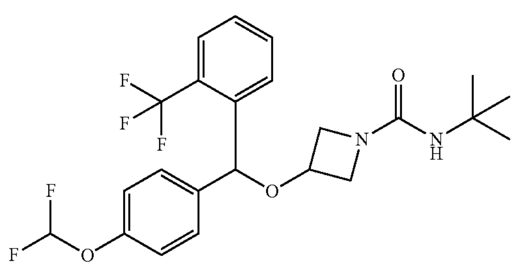 [SMILES: CC(C)(C)NC(=O)N1CC(OC(c2ccc(OC(F)F)cc2)c2ccccc2C(F)(F)F)C1] |
| 77 | 3-[2-(trifluoromethyl)-4'-(difluoromethoxy)benzhydryloxy]-N-(sec-butyl)azetidine-1-carboxamide | 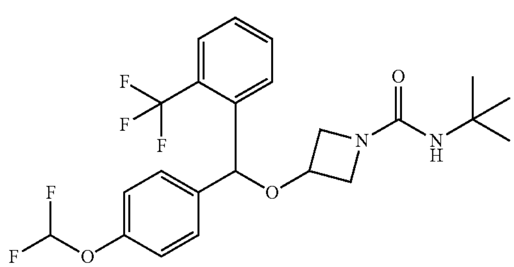 [SMILES: CC(C)(C)NC(=O)N1CC(OC(c2ccc(OC(F)F)cc2)c2ccccc2C(F)(F)F)C1] |

TABLE 1-continued

| # | Name | Structure |
|---|------|-----------|
| 78 | 3-[2-(trifluoromethyl)-4'-(difluoromethoxy)benzhydryloxy]-N-(iso-propyl)azetidine-1-carboxamide | 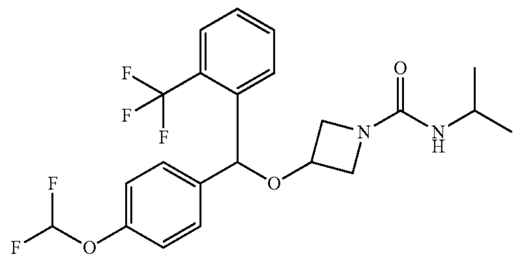 [SMILES: CC(C)NC(=O)N1CC(OC(c2ccc(OC(F)F)cc2)c2ccccc2C(F)(F)F)C1] |
| 79 | 3-[2-(trifluoromethyl)-4'-(difluoromethoxy)benzhydryloxy]-N-(cyclohexyl)azetidine-1-carboxamide | 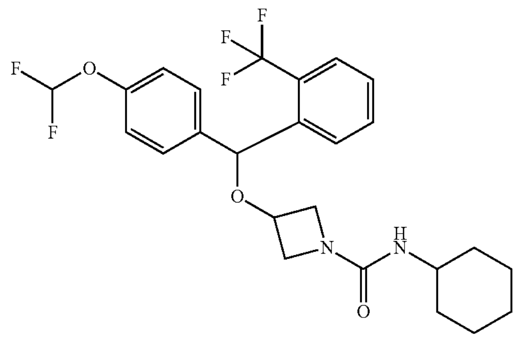 [SMILES: O=C(NC1CCCCC1)N1CC(OC(c2ccc(OC(F)F)cc2)c2ccccc2C(F)(F)F)C1] |
| 80 | 3-[2-(trifluoromethyl)-4'-(difluoromethoxy)benzhydryloxy]-N-(allyl)azetidine-1-carboxamide | 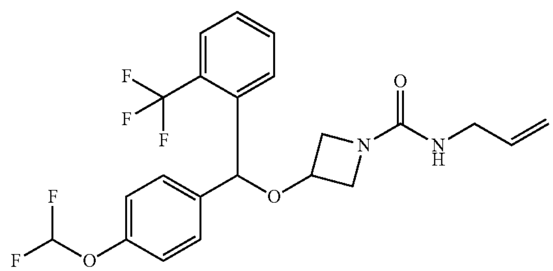 [SMILES: C=CCNC(=O)N1CC(OC(c2ccc(OC(F)F)cc2)c2ccccc2C(F)(F)F)C1] |
| 81 | 3-[2-(trifluoromethyl)-4'-fluorobenzhydryloxy]-N-(sec-butyl)azetidine-1-carboxamide | 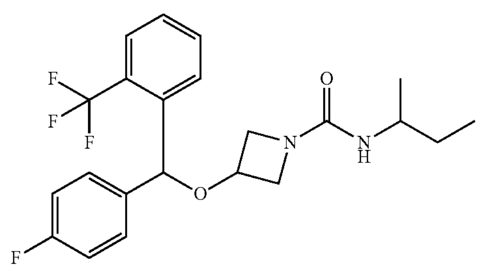 [SMILES: CCC(C)NC(=O)N1CC(OC(c2ccc(F)cc2)c2ccccc2C(F)(F)F)C1] |
| 82 | 3-[2-(trifluoromethyl)-4'-fluorobenzhydryloxy]-N-(iso-propyl)azetidine-1-carboxamide | 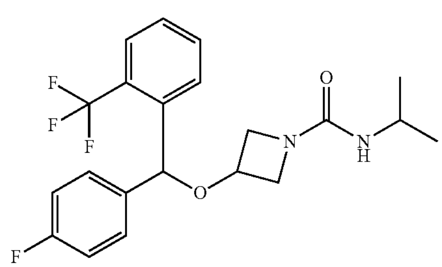 [SMILES: CC(C)NC(=O)N1CC(OC(c2ccc(F)cc2)c2ccccc2C(F)(F)F)C1] |

TABLE 1-continued

| # | Name | Structure |
|---|------|-----------|
| 83 | 3-[2-(trifluoromethyl)-4'-fluorobenzhydryloxy]-N-(S)-a-methylbenzyl]azetidine-1-carboxamide | 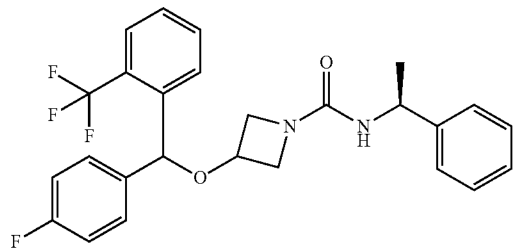 [SMILES: C[C@H](NC(=O)N1CC(OC(c2ccc(F)cc2)c2ccccc2C(F)(F)F)C1)c1ccccc1] |
| 84 | 3-[2-(trifluoromethyl)-2'-fluoro-4'-(1-piperidinyloxomethyl)benzhydryloxy]-N-(tert-butyl)azetidine-1-carboxamide | 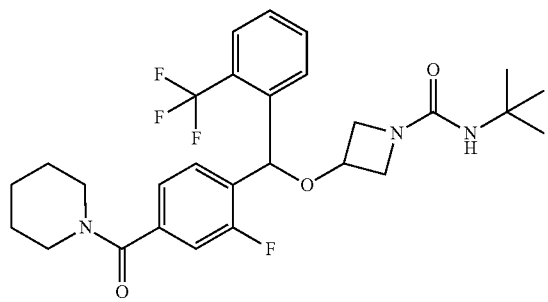 [SMILES: CC(C)(C)NC(=O)N1CC(OC(c2ccc(C(=O)N3CCCCC3)cc2F)c2ccccc2C(F)(F)F)C1] |
| 85 | 3-[2-(trifluoromethyl)-2'-fluorobenzhydryloxy]-N-(tert-butyl)azetidine-1-carboxamide | 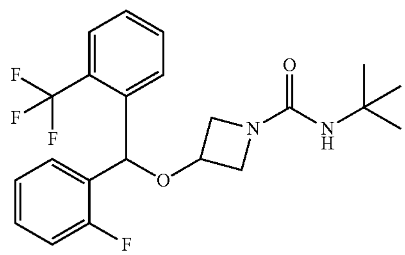 [SMILES: CC(C)(C)NC(=O)N1CC(OC(c2ccccc2F)c2ccccc2C(F)(F)F)C1] |

Formulations

Formulations described herein may comprise a CB1 inhibitor and one or more excipients. In some aspects, described herein is a CB1 inhibitor co-formulated or co-administered with one or more agents that alkalinizes the tissues or body fluids in contact with the drug when disbursed. In some instances, the CB1 inhibitor is ANEB-001. A buccal delivery or sublingual delivery is in some instances particularly useful for this aspect of the methods described herein. Without being bound by theory, alkalinizing the solution in some instances resulting in the absorption of a CB1 inhibitor is hastened as the nitrogen in a CB1 inhibitor is less likely to exist in the protonated state, where the protonated state reduces its ability to traverse biologic membranes. The use of an alkaline formulation in combination with a CB1 inhibitor treatment in some instances facilitates the improved and faster absorption of the compound, especially in buccal or sublingual delivery. Accordingly, combinations of a CB1 inhibitor with appropriate alkalinizing compounds can either modify the protonation of a CB1 inhibitor or modify the buccal or sublingual tissue to promote improved transmission of a CB1 inhibitor into the bloodstream. Similarly, surfactants, including sodium dodecyl (lauryl) sulfate, polysorbates, laureths, Brij s, and benzalkonium chloride are predominantly water-soluble compounds that form associations (micelles) in aqueous solution. These associations in some instances enhance the sublingual or transbuccal permeation of a CB1 inhibitor into the bloodstream.

The active compound (e.g., CB1 inhibitor) may be used in a pharmaceutical formulation including a pharmaceutically acceptable carrier. Accordingly, described herein are pharmaceutical formulations comprising a compound or a pharmaceutically acceptable salt, ester, prodrug or solvate thereof, together with one or more pharmaceutically acceptable carriers thereof and optionally one or more other therapeutic ingredients. The carrier(s) is "acceptable" in the sense of being compatible with the other ingredients of the formulation, the activity of the CB1 inhibitor, and not deleterious to the patient. Proper formulation is dependent upon the route of administration chosen. Any of the well-known techniques, carriers, and excipients may be used as suitable and as understood in the art (see, e.g., Remington: The Science and Practice of Pharmacy, Twenty Second Edition, Pharmaceutical Press, 2015, hereby incorporated by reference). The pharmaceutical compositions of the CB1 inhibitors described herein may be manufactured by means of conventional mixing, dissolving, granulating, dragee-making, levigating, emulsifying, encapsulating, entrapping or compression processes.

The formulations for CB1 inhibitors (e.g., ANEB-001), include those suitable for oral, parenteral (including subcutaneous, intradermal, intramuscular, intravenous, intraarticular, and intramedullary), intraperitoneal, transmucosal, transdermal, suppository or rectal, and topical (including dermal, buccal, sublingual and intraocular) administration, although the most suitable route may depend upon the condition and disorder of the patient. In some instances, such formulations reverse one or more overdose symptoms. In one embodiment, the method comprises using a composition formulated for oral, sublingual, intranasal, absorbed by suppository, or parenteral administration comprising an effective amount of a CB1 inhibitor or a salt or polymorph thereof that is effective to reverse cannabinoid overdose or one or more symptoms of overdose in a patient. In some instances, formulations are fast-acting to reverse or ameliorate an overdose, such as in an emergency or rescue situation. In some instances, fast-acting formulations include methods of administration which deliver an effective amount of a formulation comprising a CB1 inhibitor to the bloodstream in a rapid manner. In some instances, a formulation is delivered in effective concentrations in no more than 1 hr, 30 min, 15 min, 10 min, 5 min, 2 min, 1 min, 30 sec or no more than 15 sec. In some instances, a formulation is delivered in effective concentrations in 10 sec-2 hr, 30 sec-2 hr, 1 min-2 hr, 10 sec-30 sec, 10 sec-1 min, 10-sec-2 min, or 15 min-2 hr. In some instances, a fast-acting formulation is delivered via intranasal, rectal, buccal, inhalation, or transdermal routes.

The formulations may conveniently be presented in unit dosage form and may be prepared by any of the methods well known in the art of pharmacy. All methods include the step of bringing into association a compound described herein (e.g., CB1 inhibitor) or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation. In some instances, the carrier is a biopolymer, such as methyl cellulose.

Formulations of CB1 inhibitors described herein for oral administration may be presented as discrete units such as capsules, cachets or tablets each containing a predetermined amount of the active ingredient. The a CB1 inhibitor compound can be a powder or granules, a solution or a suspension in an aqueous liquid, a non-aqueous liquid, an oil-in-water liquid emulsion, or a water-in-oil liquid emulsion. a CB1 inhibitor may also be used as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricants, surface active agents or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

For buccal or sublingual administration, the compositions may take the form of tablets, lozenges, pastilles, or gels formulated in a conventional manner (Remington: The Science and Practice of Pharmacy, Twenty Second Edition, Pharmaceutical Press, 2015). Such compositions may comprise the active ingredient in a flavored basis such as with sucrose or other sweetener, and/or acceptable flavorings.

Pharmaceutically acceptable carriers (e.g., excipients) for formulations described herein (e.g., with a CB1 inhibitor) may comprise one or more polymers. In some embodiments, the pharmaceutically acceptable carrier is a polymer. Examples of polymers suitable for oral, buccal, intranasal, transdermal, thin-film, suppository or other administration include biocompatible and biodegradable polymers. Further examples of biocompatible polymers include natural or synthetic polymers such as polystyrene, polylactic acid, polyketal, butadiene styrene, styreneacrylic-vinyl terpolymer, polymethylmethacrylate, polyethylmethacrylate, polyalkylcyanoacrylate, styrene-maleic anhydride copolymer, polyvinyl acetate, polyvinylpyridine, polydivinylbenzene, polybutyleneterephthalate, acrylonitrile, vinylchloride-acrylates, polycaprolactone, poly(alkyl cyanoacrylates), poly (lactic-co-glycolic acid), and the like. In some instances, the carrier is Labrasol. In some instances, the carrier is methyl cellulose. In further embodiments, the pharmaceutically acceptable carrier comprises one or more biodegradable polymers. Use of biodegradable polymers provides the advantages of using a formulation that will eventually disintegrate, which facilitates release of the benzofuran compound and elimination of the carrier in vivo. However, benzofuran compounds can also be released from the matrix of non-biodegradable polymers as a result of gradual efflux from channels within the polymer matrix, including those formed by soluble materials included in the polymer matrix.

Examples of biodegradable polymers include polylactide polymers include poly(D,L-lactide)s; poly(lactide-co-glycolide) (PLGA) copolymers; polyglycolide (PGA) and polydioxanone; caprolactone polymers; chitosan; hydroxybutyric acids; polyanhydrides and polyesters; polyphosphazenes; and polyphosphoesters. In some instances, the biodegradable polymer for use in the nanoparticles is poly-(D, L-lactide-co-glycolide).

Functionalized poly (D,L-lactide)s can also be used as biodegradable polymers in the nanoparticles described herein. Examples of functionalized poly(D,L-lactide)s include poly(L-lactide), acrylate terminated; poly(L-lactide), amine terminated; poly(L-lactide), azide terminated; poly(L-lactide), 2-bromoisobutyryl terminated; poly(L-lactide), 2-bromoisobutyryl terminated; poly(L-lactide) 4-cyano-4-[(dodecylsulfanylthiocarbonyl)sulfanyl]pentonate; poly(L-lactide)N-2-hydroxyethylmaleimide terminated; poly(L-lactide) 2-hydroxyethyl, methacrylate terminated; poly(L-lactide), propargyl terminated; or poly(L-lactide), thiol terminated.

Other biodegradable polymers that can be used in the nanoparticles include AB-39-eblock copolymers such as poly(ethylene glycol) methyl ether-block-poly(D,L-lactide); poly(ethylene glycol) methyl ether-block-poly(lactide-co-glycolide) PEG; poly(ethylene glycol)-block-poly(.epsilon.-caprolactone) methyl ether PEG; and polypyrrole-blockpoly(caprolactone). Further biodegradable polymers include ABA triblock copolymers such as polylactide-block-poly(ethylene glycol)-block-polylactide PLA; poly(lactide-co-glycolide)-block-poly(ethylene glycol)-block-poly(lactide-co-glycolide); poly(lactide-co-caprolactone)-block-poly (ethylene glycol)-block-poly(lactide-co-caprolactone); polycaprolactone-block-polytetrahydrofuran-block-poly-caprolactone; and polyglycolide-block-poly(ethylene glycol)-block-polyglycolide PEG.

Biodegradable polymers also include various natural polymers. Examples of natural polymers include polypeptides including those modified non-peptide components, such as saccharide chains and lipids; nucleotides; sugar-based biopolymers such as polysaccharides; cellulose; carbohydrates and starches; dextrans; lignins; polyamino acids; adhesion proteins; lipids and phospholipids (e.g., phosphorylcholine). In some embodiments, the polymer is a cellulose derivative such as hydroxypropyl methylcellulose polymers. Hydroxypropyl methyl cellulose (HPMC) is a non-ionic cellulose ether made through a series of chemical processes, with the natural polymer cellulose as the raw material. The product is a non-ionic cellulose ether in the shape of white powder, odorless and tasteless. HPMC is also known as hypromellose, is a methylcellulose modified with a small amount of propylene glycol ether groups attached to the anhydroglucose of the cellulose.

CB1 inhibitors described herein may be formulated with one or more pharmaceutically active agents. In some embodiments described herein, the CB1 inhibitor is formulated with naloxone or an opioid antidote. In some instances, an opioid antidote or opioid antagonist includes nalmefene or nalorphine. These can be administered with a Luer-Jet or Luer Lock Prefilled Syringe of 2 mg/2 mL naloxone hydrochloride. The IMS Luer-Jet™ system is a needleless prefilled emergency syringe. In some instances, the CB1 inhibitor is administered with flumazenil or other benzodiazepine antagonist. And similarly, in some instances the CB1 inhibitor is administered with both an opioid and a benzodiazepine antagonist in a single formulation. In another aspect, devices and methods described herein provide an overdose rescue pen that an emergency responder or others can use to treat an unresponsive person suspected of a drug overdose where the drug(s) in question are unknown. Said pen in some instances includes one or more of a narcotic antagonist, a benzodiazepine antagonist, and a cannabinoid antagonist such as ANEB-001, or a CB1 neutral antagonist. Formulations described herein are in some instances are configured for IV, IM, subcutaneous or other injection, or for intranasal delivery. Intranasal formulations comprising certain polymers in some instances increase the residence time of active compounds on the mucosal membranes. Similarly, the pH of the formulation and/or the ionization state of the active compound(s) are in some instances taken into consideration for more effective transport across the nasal mucosa.

A formulation described herein may comprise a CB1 inhibitor and one or more active agents. In some instances, a CB1 inhibitor is administered with an active agent in a 0.1:1, 0.2:1, 0.5:1, 1:1, 1.5:1, 2:1, 5:1, or 10:1 (w/w). In some instances, a CB1 inhibitor is administered with an active agent in a 0.1:1, 0.2:1, 0.5:1, 1:1, 1.5:1, 2:1, 5:1, or 10:1 (molar ratio). In some instances, the CB1 inhibitor is administered with the one or more active agents as a single formulation. In some instances, the CB1 inhibitor is administered with the one or more active agents as two or more formulations. A CB1 inhibitor may be administered in combination with one or more active agents. In some instances, the active agent is an anxiolytic agent. In some instances, the active agent is a cannabinoid. In some instances, the cannabinoid is cannabidiol (CBD). In some instances, the active agent is CBG (Cannabigerol), CBD (Cannabidiol), CBC (Cannabichromene), CBGV (Cannabigerivarin), THCV (Tetrahydrocannabivarin), CBDV (Cannabidivarin), or CBCV (Cannabichromevarin).

Formulations comprising a CB1 inhibitors (such as ANEB-001) may comprise one or more active agents (e.g., CBD). In some instances, a formulation comprises about 1 mg, 2 mg, 5 mg, 10 mg, 25 mg, 40 mg, 60 mg, 75 mg, 100 mg, 125 mg, or 150 mg of ANEB-001 and 0.5, 1, 2, 5, 10, 20, 50, 75, 100, 150, 300, 500, or 800 mg of CBD. Formulations comprising a CB1 inhibitors (such as ANEB-001) may comprise one or more active agents (e.g., CBD). In some instances, a formulation comprises about 10-150 mg of ANEB-001 and 0.5, 1, 2, 5, 10, 20, 50, 75, 100, or 150 mg of CBD. In some instances, a formulation comprises about 50-150 mg of ANEB-001 and 0.5, 1, 2, 5, 10, 20, 50, 75, 100, 150, 300, 500, or 800 mg of CBD. In some instances, a formulation comprises about 60-120 mg of ANEB-001 and 0.5, 1, 2, 5, 10, 20, 50, 75, 100, or 150, 300, 500, or 800 mg CBD. In some instances, a formulation comprises about 10-150 mg of ANEB-001 and 5-800 mg of CBD. In some instances, a formulation comprises about 1 mg, 2 mg, 5 mg, 10 mg, 25 mg, 40 mg, 60 mg, 75 mg, 100 mg, 125 mg, or 150 mg of ANEB-001 and 5-800 mg of CBD.

Methods of Treatment

Compositions and formulations described herein may be administered as single or multiple doses. In one aspect, described herein are methods of using a CB1 inhibitor (e.g., ANEB-001) as a single dose, one-time treatment for overdose of THC or SCs, or both. The overdose can also be from consumption of cannabis, a synthetic cannabinoid, or any compound that is an agonist at the CB1 receptor. In some instances, methods described herein include treatments to children who inadvertently consume cannabis or cannabinoid edibles. In related aspects, any suspected overdose patient that presents as mentally disoriented or psychotic or cannot articulate the nature of their condition or the substances that have been ingested or administered can be treated with a CB1 inhibitor. In some instances, a THC or SC overdose is treated by administration of a CB1 inhibitor and one or more active agents (e.g., opioid antagonist, benzodiazepine antagonist, cannabinoid, or other active agent). In some instances, the CB1 inhibitor and one or more active agents are administered as a single formulation.

Described herein are methods of treating patients for one or more of the following: a CB1 antagonist (e.g., ANEB-001) formulated for oral, intravenous (IV), intramuscular (IM), subcutaneous (SC), endotracheal, sublingual, buccal, intralingual, submental, transdermal, and intranasal administration. In some instances, a CB1 inhibitor is formulated in an injector pen for on-site administration to an overdose patient as well as the use of a CB1 inhibitor by emergency responders to treat THC or SC overdose outside of the hospital. The methods described herein also include the use of a CB1 inhibitor to treat cannabinoid hyperemesis syndrome and the use of various formulations and administration methods for that treatment, including the use of a CB1 inhibitor in suppository form to treat cannabinoid hyperemesis syndrome. In some instances, a CB1 inhibitor is formulated for rapid nasal injection.

In some instances, CB1 antagonists prevent, treat or reduce the severity of various medical conditions and symptoms, including, but not limited to obesity, appetite disorder, another metabolic disorder, drug addiction and/or mental illness. In some instances, CB1 antagonists are used for the treatment of: addiction, alcoholism, Alzheimer's disease, anorexia nervosa, anxiety disorder, appetite disorders, attention deficit hyperactivity disorder, bipolar disorder, bulimia nervosa, cancer, cardiovascular disorders, central nervous system disease, cerebral ischemia, cerebral apoplexy, chemotherapy induced emesis, cocaine addiction, cognitive disorder, dementia, demyelination related disorders, diabetes, diabetic neuropathy, diarrhea, drug dependence, dystonia, eating disorder, emesis, epilepsy, female sexual dysfunction, functional bowel disorder, gastrointestinal disorders, gastric ulcers, generalized anxiety disorder, glaucoma, headache, Huntington's disease, impulse control disorders inflammation, irritable bowel syndrome, male sexual dysfunction, major depressive disorder, memory disorders menopause, migraine, muscle spasticity, multiple sclerosis, myalgia, nausea, neuralgia, neurodegenerative disorders, neuroinflammatory disorders, neuropathic pain, obesity, obsessive compulsive disorder, osteoarthritis, pain, panic disorder, Parkinson's disease, plaque sclerosis, premature ejaculation, premenstrual syndrome, psychosexual disorder, psychosis, rheumatoid arthritis, septic shock, schizophrenia, sexual disorders, sleep disorder, spinal cord injury, stroke, Tourette's syndrome, traumatic brain injury, tremor, urinary incontinence, and viral encephalitis.

The methods described herein include pre-exposure prophylaxis treatments. The long term effects of CB1 antagonism, which in some instances includes anhedonia, potentially makes them unsuitable for chronic use. However, in the same way an alcoholic might consume disulfiram before entering a situation when tempted to consume alcohol, one can take a CB1 antagonist, such as ANEB-001, before encountering a situation where they may likely be exposed to or tempted to ingest THC or SCs or both. Similarly, in some instances, a CB1 inhibitor is used to prevent effects from second hand smoke from marijuana. The method of using a CB1 inhibitor in some instances includes use by someone who wishes to gain acceptance to a situation or group by smoking marijuana or SCs, but also wants to remain mentally alert, such as during an undercover police or law enforcement investigation.

The methods described herein include use of a CB1 inhibitor to treat cannabinoid hyperemesis syndrome. In one aspect, the use of the CB1 inhibitor in a suppository form is used to treat cannabinoid hyperemesis syndrome.

Methods described herein may be used to treat a patient with a known or suspected acute drug overdose. In some instances, this is determined by the judgement of a qualified healthcare professional or emergency medical technician. In some instances, a lack of or reduced response to prior overdose treatments indicates a potential cannabinoid overdose. Such a patient is in some instances subsequently treated using the CB1 inhibitors described herein. In some instances, a patient is treated with a prior treatment comprising administration of an opiate antagonist, activated charcoal, or emetic. In some instances, the prior treatment is orogastric lavage or whole bowel irrigation.

A CB1 inhibitor may be administered after confirmation of a cannabinoid overdose by one or more testing methods. In some instances, the testing method is a blood test. In some instances, the blood test comprises determination of the cannabinoid plasma concentration. In some instances, a patient is administered a CB1 inhibitor (e.g., ANEB-001) when his or her cannabinoid plasma concentration is at least 25, 50, 125, 150, 175, 200, 225, 250, 275, 300, 325, or at least 350 ug/L. In some instances, a patient is administered a CB1 inhibitor (e.g., ANEB-001) when his or her cannabinoid plasma concentration is 25-300 ug/L, 50-300 ug/L, 75-300 ug/L, 100-300 ug/L, 125-300 ug/L, or 200-400 ug/L.

A CB1 inhibitor (e.g., ANEB-001) may be administered to obtain diagnostic information about whether a patient is suffering from a cannabinoid or synthetic cannabinoid overdose. If a patient's mental state fails to improve upon administration of a CB1 inhibitor, other etiologies of confusion or altered mental state in some instances are considered, including intoxication with other substances, psychiatric illnesses, metabolic conditions and inflammatory, infectious or traumatic conditions of the brain. Treatment with a CB1 inhibitor in some instances is used for diagnostic purposes.

A CB1 inhibitor may be administered in combination with one or more active agents. In some instances, the active agent is an anxiolytic agent. In some instances, the active agent is a cannabinoid. In some instances, the cannabinoid is cannabidiol (CBD). In some instances, the active agent is CBG (Cannabigerol), CBD (Cannabidiol), CBC (Cannabichromene), CBGV (Cannabigerivarin), THCV (Tetrahydrocannabivarin), CBDV (Cannabidivarin), or CBCV (Cannabichromevarin).

In some instances, a CB1 inhibitor is administered with an active agent in a 0.1:1, 0.2:1, 0.5:1, 1:1, 1.5:1, 2:1, 5:1, or 10:1 (w/w). In some instances, a CB1 inhibitor is administered with an active agent in a 0.1:1, 0.2:1, 0.5:1, 1:1, 1.5:1, 2:1, 5:1, or 10:1 (molar ratio). In some instances, the CB1 inhibitor is administered with the one or more active agents as a single formulation. In some instances, the CB1 inhibitor is administered with the one or more active agents as two or more formulations.

After administration of a CB1 inhibitor (e.g., ANEB-001) described herein, a patient may be monitored for improvement. Monitoring in some instances comprises heart rate monitoring, respiration monitoring, or measures such as patient cognitive function or behavior. In some instances, monitoring comprises patient-reported feelings or answers to verbal or written interrogatories.

Dosages

CB1 inhibitors may be dosed in various amounts. In some instances, the CB1 inhibitor is dosed at about 1, 2, 5, 10, 25, 40, 50, 75, 90, 100, or about 150 mg. In some instances, the CB1 inhibitor is dosed at no more than 1, 2, 5, 10, 25, 40, 50, 75, 90, 100, or no more than 150 mg. In some instances, the CB1 inhibitor is dosed at least at 1, 2, 5, 10, 25, 40, 50, 75, 90, 100, or at least 150 mg. In some instances, the CB1 inhibitor is dosed at 1-200, 1-100, 1-50, 2-100, 5-100, 10-150, 10-200, 20-120, 50-125, 50-200, or 75-150 mg. In some instances, the CB1 inhibitor is dosed orally. In some instances, the CB1 inhibitor is dosed rectally.

CB1 inhibitors (such as ANEB-001) may be administered in an oral dosage form. In some instances, ANEB-001 is dosed (oral) at 1 mg, 2 mg, 5 mg, 10 mg, 25 mg, 40 mg or more, typically taken once, or once daily. ANEB-001 at 30 mg/kg to 10 mg/kg i.p. is in some instances administered subcutaneously. Similarly, a single dose of ANEB-001 i.p. at 0.1 mg/kg is in some instances used. For example, a CB1 inhibitor test employing forty-two male volunteers to receive one of three oral drug regimens, 40 mg daily for 15 days, placebo for 14 days, then 90 mg on day 15, or placebo for 15 days can be used test effectiveness. Oral dosages of ANEB-001 are in some instances selected from one or more of 1 mg, 2 mg, 5 mg, 10 mg, 25 mg, or 40 mg once daily. In some instances, oral dosages of ANEB-001 are about 1 mg, 2 mg, 5 mg, 10 mg, 25 mg, 40 mg, 50 mg, 60 mg, 75 mg, 90 mg, or about 100 mg. While preferably delivered as an acute therapy, ANEB-001 is administered daily for up to 2, 4, 6, 10, 12, 15, 20, 25, or up to 28 days. In some instances, ANEB-001 is administered as a single acute dosage. CB1 inhibitors (such as ANEB-001) may be administered with one or more active agents, such as CBD. In some instances, a CB1 inhibitor is administered with 0.5, 1, 2, 5, 10, 20, 50, 75, 100, or 150 mg of CBD.

Definitions

As used herein, the term "about" is intended to qualify the numerical values which it modifies, denoting such a value as variable within a range. When no range, such as a margin of error or a standard deviation to a mean value given in a chart or table of data, is recited, the term "about" should be understood to mean the greater of the range which would encompass the recited value and the range which would be included by rounding up or down to that figure as well, considering significant figures, and the range which would encompass the recited value plus or minus 20%.

As used herein, the term "agonist" refers to a moiety that interacts with, and activates, a receptor and thereby initiates a physiological or pharmacological response characteristic of that receptor.

As used herein, the term "antagonist" refers to a compound that binds to a receptor, such as CB1, but which does not activate the intracellular response(s) initiated by an active agonist compound of the receptor. The antagonist can thereby inhibit the intracellular responses that would be elicited by an agonist or partial agonist if present. An antagonist does not diminish the baseline intracellular response in the absence of an agonist or partial agonist. The term "inverse agonist" refers to a moiety that binds to the endogenous form of the receptor or to the constitutively activated form of the receptor and which inhibits the baseline intracellular response initiated by the active form of the receptor below the normal base level of activity which is observed in the absence of an agonist or partial agonist. It is noted that under certain conditions a compound can behave like an antagonist while under other conditions it can behave as an inverse agonist. Functionally, both an antagonist and an inverse agonist can block and/or reverse the effects of an agonist or partial agonist. In some instances, a CB1 inhibitor includes compounds which act as antagonists or inverse agonists. In some instances, the term "neutral antagonist" is an antagonist that does not change the baseline response level of the receptor when it binds to receptor. In some instances, a neutral antagonist comprises ANEB-001.

As used herein, symptom(s) of cannabinoid overdose is "apparent" or "suspected" when, in the judgment of a trained healthcare provider or emergency responder, the patient has one or more symptom(s) associated with a cannabinoid overdose. In some instances, a cannabinoid overdose is suspected from an absence or reduced response to other overdose related medical treatments (e.g., opioid antagonists, antipsychotics, or other overdose treatment).

As used herein, reversal of symptom(s) of cannabinoid overdose is "apparent" when, in the judgment of a trained healthcare provider or emergency responder, the symptom (s) have been reduced or abated to a noticeable degree. Such a provider may use any appropriate measure to quantify the reversal of symptom(s), e.g., a visual analog scale for self-reporting, a heart rate monitor for tachycardia, an improved affect, etc. "Apparent" reversal of symptom(s) includes, but need not extend to, complete reversal.

As used herein, the term "cannabinoid" is synonymous with "cannabinoid receptor agonist" and refers to a compound which binds to and activates a cannabinoid receptor. The term includes both natural and synthetic compounds.

As used herein, the term "synthetic cannabinoid" ("SC") means a non-naturally-occurring cannabinoid. Most SCs are lipid-soluble, non-polar, small molecules that are fairly volatile, and often have a side-chain of 5-9 saturated carbon atoms. SCs are associated with psychotropic activity from binding CB1 receptors. There are at least five major structural categories for synthetic cannabinoids: classical cannabinoids, non-classical cannabinoids, hybrid cannabinoids, aminoalkylindoles (and their analogues), and eicosanoids. Classical cannabinoids are analogs of THC that are based on a dibenzopyran ring; examples include nabilone, dronabinol, and the (−)-1,1-dimethylheptyl analog of 11-hydroxy-$\Delta$8-tetrahydrocannabinol. Non-classical cannabinoids include cyclohexylphenols such as cannabicyclohexanol. Hybrid cannabinoids have a combination of classical and non-classical cannabinoid structural features. Aminoalkylindoles are structurally dissimilar to THC and include naphthoylindoles such as 1-pentyl-3-(1-naphthoyl)indole, phenylacetylindoles such as 1-pentyl-3-(2-methoxyphenylacetyl)indole (JWH-250), and benzoylindoles such as 1-[(N-methylpiperidin-2-yl)methyl]-3-(2-iodobenzoyl)indole; they are the most common SCs found in SC blends due to relative ease of synthesis. Other compounds structurally similar to aminoalkylindoles include naphthoylpyrroles, naphthylmethylindenes, phenylacetylindoles/benzoylindoles, tetramethylcyclopropylindoles, adamantoylindoles, indazole carboxamides, indolecarboxylates, and quinolinyl esters. Eicosanoid SCs are analogs of endocannabinoids such as anandamide. In some instances, SCs are CB1 activators, such as agonists.

As used herein, the term "cannabinoid receptor antagonist" or "CB1 antagonist" refers to a compound that binds to and blocks or dampens the normal biological function of the CB1 receptor and its signaling. This activity can occur in the presence of a natural or synthetic agonist or partial agonist. The term includes cannabinoid receptor antagonists that are selective or nonselective for the CB1 receptor subtype.

EXAMPLES

Example 1: In Vivo Model of CB1 Antagonist Efficacy

Reversal of THC-induced hypolocomotion in mice: Six C57 mice (Charles River, Wilmington, Mass.) were administered $\Delta$9-tetrahydrocannabinol (THC) 3 mg/kg ip, 10 min pre-test. The mice exhibited reduced locomotor activity when placed in automated locomotor activity cages for 15 min. In this apparatus, four qualitatively different measures of locomotor activity are automatically scored. In a preliminary screen to identify active CB1 antagonists, ANEB-001 (compound 1) given orally at a dose of 30 mg/kg and 30 min pre-test, significantly reversed the action of THC on the total active time parameter of these locomotor measures (FIG. 1). The magnitude of the effect is similar to that elicited by rimonabant given at 3 mg/kg po, and given 30 min pre-test.

Repeated dose (28 day) toxicity studies were conducted using ANEB-001 in two species, rat and primate, selected on the basis of acceptable bioavailability and comparison of metabolite profiles with those in human liver microsomes. No adverse effects were observed at the highest dose tested in the rat, therefore the no observed adverse effect level in the rat was 75 mg/kg/day. Dose levels of 75 mg/kg/day were associated with hepatic changes consistent with an adaptive response to repeated administration of high doses of ANEB-001 to rats.

In repeat dose (28 day) toxicity studies no adverse effects were observed at the highest dose level studied in the cynomolgus monkey, 160 mg/kg/day.

Example 2: In Vivo Single Ascending Dose Pharmacokinetics in Humans

Figure 2:
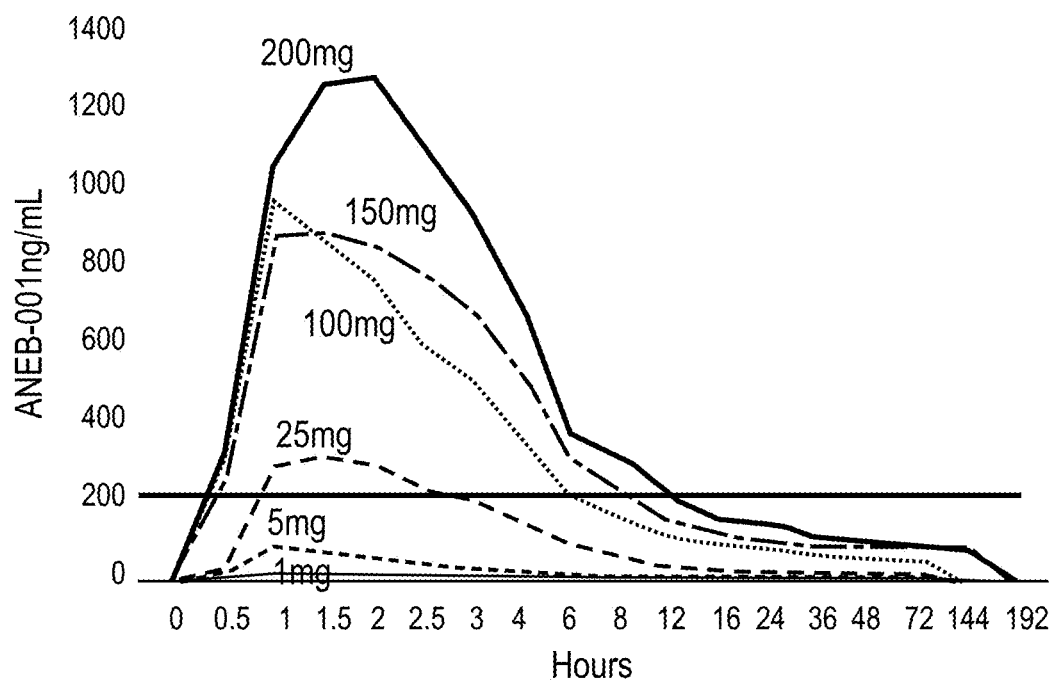
FIG. 2 illustrates a plot of a single ascending oral dose study in humans of ANEB-001. Plasma concentrations (ng/mL) of ANEB-001 are plotted against time.

Human subjects were assigned to six different dosage groups of ANEB-001. Groups assigned to receive dosages of 1 mg, 5 mg, 25 mg, 100 mg, or 200 mg had six subjects each, and the 150 mg dosage group had four subjects. ANEB-001 was administered orally to subjects in each group, and the plasma concentration of ANEB-001 in each subject was measured as a function of time after dosing (FIG. 2). ANEB-001 had a $T_{max}$ of approximately 1-1.6 hours, and a terminal elimination half-life up to 19 days.

Example 3: Treatment of THC Overdose

A patient admitted to the emergency room is diagnosed with acute THC poisoning from overconsumption of cannabinoid products, such as edibles. The patient is administered a 75 mg oral dose of a CB1 inhibitor, such as ANEB-001, and monitored for signs of improvement (heart rate, cognitive response, etc.).

Example 4: Fast Administration for Treatment of THC Overdose

A human subject diagnosed or suspected of acute THC poisoning from overconsumption of cannabinoid products is treated by a clinician or first responder with a fast-acting nasal formulation comprising a CB1 inhibitor (e.g., ANEB-001) via nasal injector. The fast-acting nasal formulation is designed to provide effective amounts of the CB1 inhibitor in no more than 10 minutes.

Example 5: Combination Treatment of THC Overdose

A patient admitted to the emergency room is diagnosed with acute THC poisoning from overconsumption of cannabinoid products, such as edibles. The patient is administered a formulation comprising a 75 mg oral dose of a CB1 inhibitor such as ANEB-001 and CBD (150 mg) and monitored for signs of improvement (heart rate, cognitive response, etc.).

The description and examples presented above and the contents of the application define and describe examples of the many combinations, apparatus, and methods that can be produced or used according to the teachings here. None of the examples and no part of the description should be taken as a limitation on the scope of the inventions or of the meaning of the following claims.

What is claimed is:

1. A method of using a pharmaceutical composition comprising a CB1 inhibitor, the method comprising orally administering to a patient an effective amount of the CB1 inhibitor and a pharmaceutically acceptable carrier or excipient, wherein the patient has an acute drug overdose reaction, wherein the CB1 inhibitor has the structure:

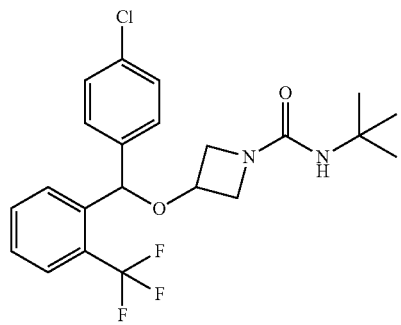 [SMILES: CC(C)(C)NC(=O)N1CC(OC(c2ccc(Cl)cc2)c2ccccc2C(F)(F)F)C1]

or a pharmaceutically acceptable salt thereof, wherein the dose of the CB1 inhibitor is 50 mg to 300 mg, and wherein the amount of CB1 inhibitor in the bloodstream of the patient reaches at least 200 ng/mL within one hour after oral administration.

2. The method of claim 1, wherein the patient shows signs of an acute cannabinoid overdose.

3. The method of claim 2, wherein the acute cannabinoid overdose is caused by a compound from the *Cannabis* genus.

4. The method of claim 2, wherein the acute cannabinoid overdose is caused by a synthetic cannabinoid.

5. The method of claim 2, wherein the acute cannabinoid overdose is caused by oral ingestion of cannabinoids or synthetic cannabinoids.

6. The method of claim 1, wherein the patient shows signs of cannabinoid hyperemesis syndrome.

7. The method of claim 1, wherein the method further comprises treatment for drug overdose prior to treatment with the CB1 inhibitor.

8. The method of claim 7, wherein the prior treatment comprises one or more of administration of an opiate antagonist, activated charcoal, or emetic.

9. The method of claim 1, wherein the method further comprises a diagnostic test prior to treatment with the CB1 inhibitor.

10. The method of claim 9, wherein the diagnostic test is a blood test.

11. The method of claim 1, wherein the patient has a cannabinoid plasma concentration of at least 50 µg/L.

12. The method of claim 1, wherein the patient has a cannabinoid plasma concentration of 50 µg/L to 300 µg/L.

13. The method of claim 1, wherein the dose of the CB1 inhibitor is 50 mg to 200 mg.

14. The method of claim 1, wherein the dose of the CB1 inhibitor is 75 mg to 200 mg.

15. The method of claim 1, wherein the CB1 inhibitor has the structure:

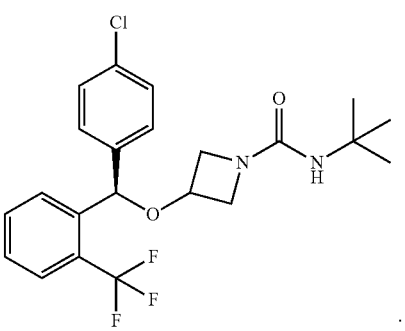 [SMILES: CC(C)(C)NC(=O)N1CC(O[C@H](c2ccc(Cl)cc2)c2ccccc2C(F)(F)F)C1]

16. The method of claim 1, wherein the amount of CB1 inhibitor in the bloodstream of the patient reaches at least 200 ng/mL within 30 minutes after oral administration.

* * * * *